United States Patent
Neikirk et al.

(10) Patent No.: US 9,291,586 B2
(45) Date of Patent: Mar. 22, 2016

(54) PASSIVE WIRELESS SELF-RESONANT SENSOR

(71) Applicant: Board of Regents, The University of Texas System, Austin, TX (US)

(72) Inventors: Dean P. Neikirk, Austin, TX (US); Praveenkumar Pasupathy, Austin, TX (US); Sheng Zhang, Austin, TX (US); Brad Leonhardt, Austin, TX (US); John G. Ekerdt, Austin, TX (US); Brian A. Korgel, Austin, TX (US); Vincent C. Holmberg, Seattle, WA (US); Catherine D. Shipman, Reston, TX (US); Timothy D. Bogart, Oxford (GB); Aaron Chockla, Chicago, IL (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/398,315

(22) PCT Filed: May 5, 2013

(86) PCT No.: PCT/US2013/039604
§ 371 (c)(1),
(2) Date: Oct. 31, 2014

(87) PCT Pub. No.: WO2013/169606
PCT Pub. Date: Nov. 14, 2013

(65) Prior Publication Data
US 2015/0123678 A1 May 7, 2015

Related U.S. Application Data

(60) Provisional application No. 61/643,242, filed on May 5, 2012.

(51) Int. Cl.
G01R 27/32 (2006.01)
G01N 27/04 (2006.01)
G01N 27/08 (2006.01)

(52) U.S. Cl.
CPC ............... G01N 27/04 (2013.01); G01N 27/08 (2013.01)

(58) Field of Classification Search
CPC ..... G01N 27/04; G01N 27/08; G01N 27/023; G01R 33/0023; B82Y 30/00; G01D 5/24
USPC .......................................... 324/636; 205/778
See application file for complete search history.

(56) References Cited

U.S. PATENT DOCUMENTS

| | | | | |
|---|---|---|---|---|
| 4,114,606 A | * | 9/1978 | Seylar | A61B 5/031 165/DIG. 401 |
| 5,091,704 A | * | 2/1992 | Kopera | G01N 27/023 123/575 |

(Continued)

FOREIGN PATENT DOCUMENTS

WO 00/79497 A1 12/2000

OTHER PUBLICATIONS

Russian Federal Service for Intellectual Property, Patent and Trademarks (ISA), International Search Report and Written Opinion for PCT/US2013/039604 dated Aug. 29, 2013. (7 pp.).

*Primary Examiner* — Benjamin M Baldridge
(74) *Attorney, Agent, or Firm* — Daniel J. Chalker; Edwin S. Flores; Chalker Flores, LLP

(57) ABSTRACT

A sensor for detecting one or more materials includes a substrate, a passivation layer formed on the substrate, a self-resonant structure and a high surface area material disposed on the passivation layer. The self-resonant structure includes a planar spiral inductor and a plurality of planar interdigitated capacitor electrodes disposed within the passivation layer. The planar spiral inductor includes an electrically conductive trace formed on the substrate in a planar spiral pattern having at least two turns and an inter-winding space between parallel segments of the electrically conductive trace. The plurality of planar interdigitated capacitor electrodes are electrically connected to the electrically conductive trace of the planar spiral inductor and formed on the substrate within the inter-winding space of at least one outermost turn of the planar spiral inductor. The high surface area material includes a conformal polymer coating to increase a sensitivity to the one or more materials.

20 Claims, 33 Drawing Sheets

(56) References Cited

U.S. PATENT DOCUMENTS

| | | | | |
|---|---|---|---|---|
| 5,594,342 A * | 1/1997 | Brey | G01R 33/34 324/318 |
| 5,619,140 A * | 4/1997 | Brey | G01R 33/34 29/593 |
| 5,704,352 A * | 1/1998 | Tremblay | A61B 5/0031 600/300 |
| 6,194,900 B1 * | 2/2001 | Freeman | G01R 33/302 324/318 |
| 6,939,299 B1 | 9/2005 | Petersen et al. | |
| 8,104,358 B1 * | 1/2012 | Jia | G01B 7/22 73/780 |
| 8,236,164 B2 * | 8/2012 | Gustafsson | G01N 27/223 204/430 |
| 2001/0016683 A1 * | 8/2001 | Darrow | A61B 5/0031 600/347 |
| 2003/0071763 A1 * | 4/2003 | McKinzie, III | H01Q 9/0421 343/909 |
| 2005/0200359 A1 * | 9/2005 | Withers | G01R 33/341 324/318 |
| 2012/0092222 A1 * | 4/2012 | Kato | G08B 13/00 343/742 |
| 2012/0156688 A1 * | 6/2012 | McAlpine | B82Y 15/00 435/7.1 |
| 2012/0297888 A1 * | 11/2012 | Nagarajan | G01B 7/16 73/774 |
| 2012/0302861 A1 * | 11/2012 | Marshall | A61B 5/0031 600/398 |

\* cited by examiner

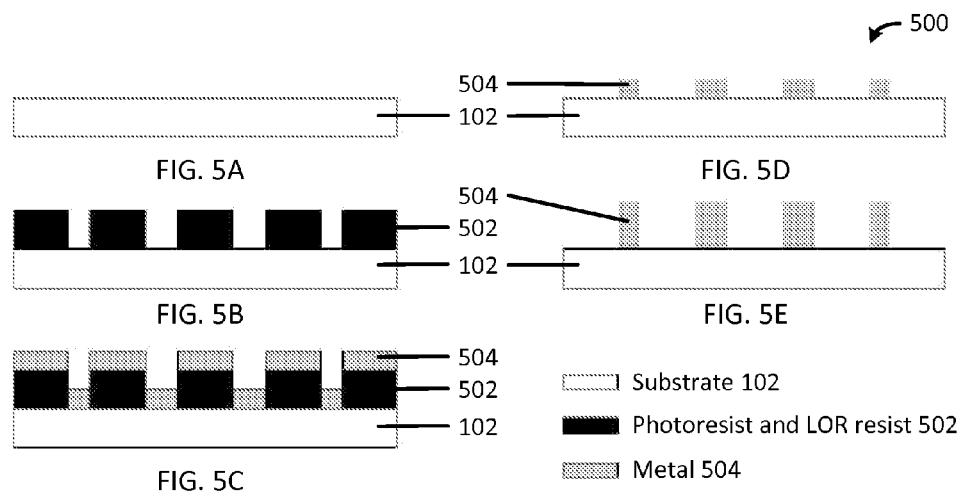
FIG. 5A
FIG. 5B
FIG. 5C
FIG. 5D
FIG. 5E
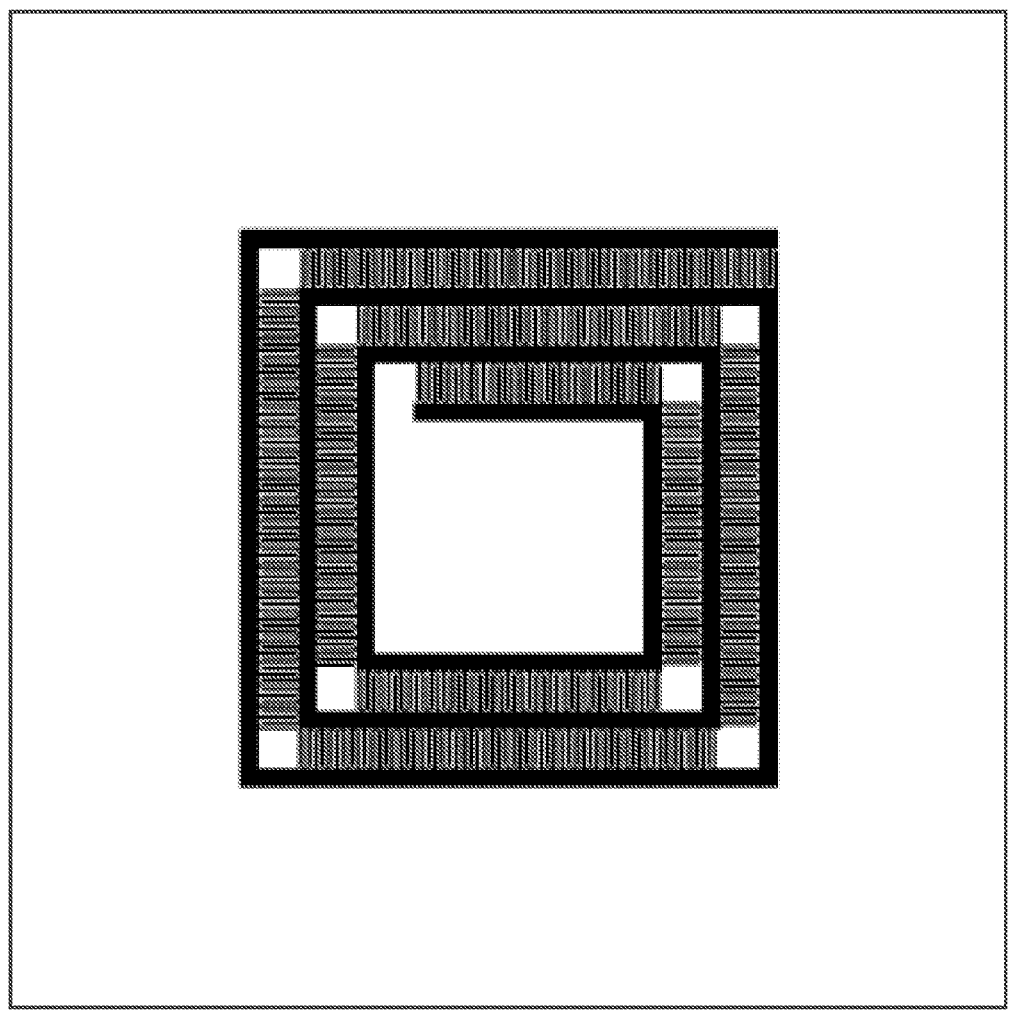
FIG. 6

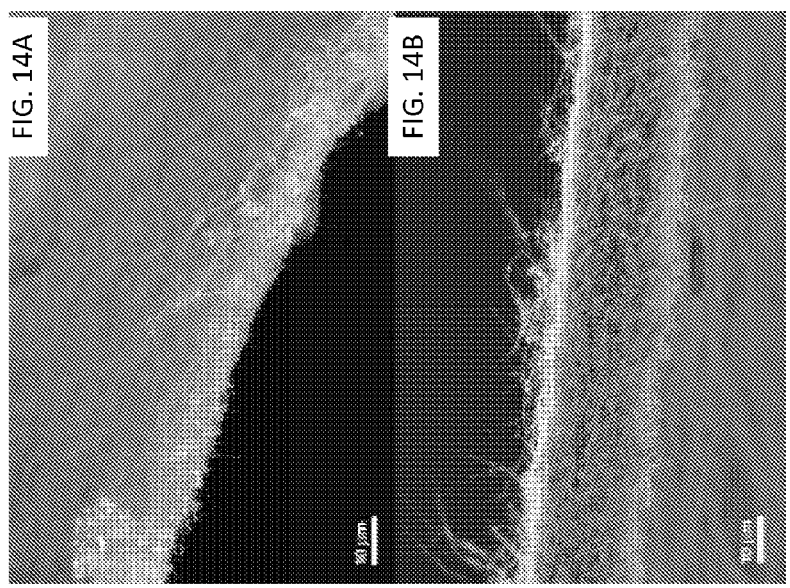
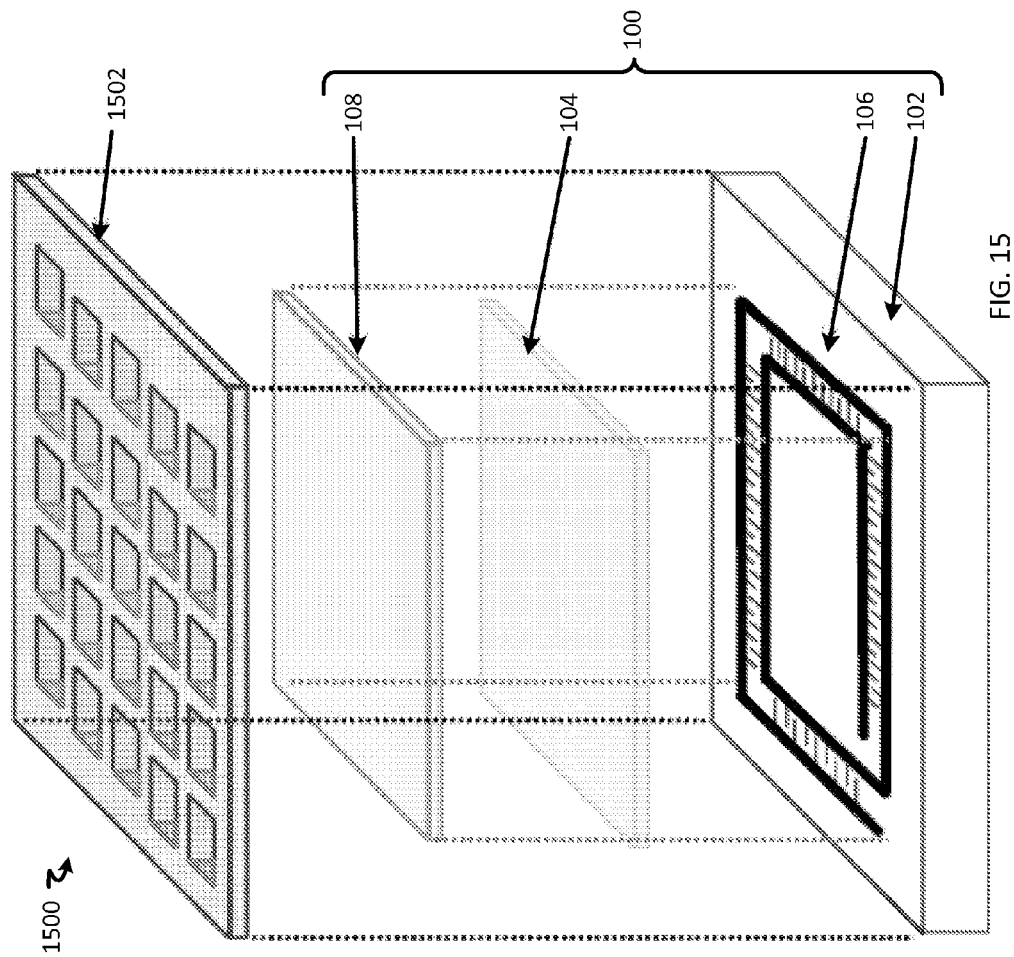

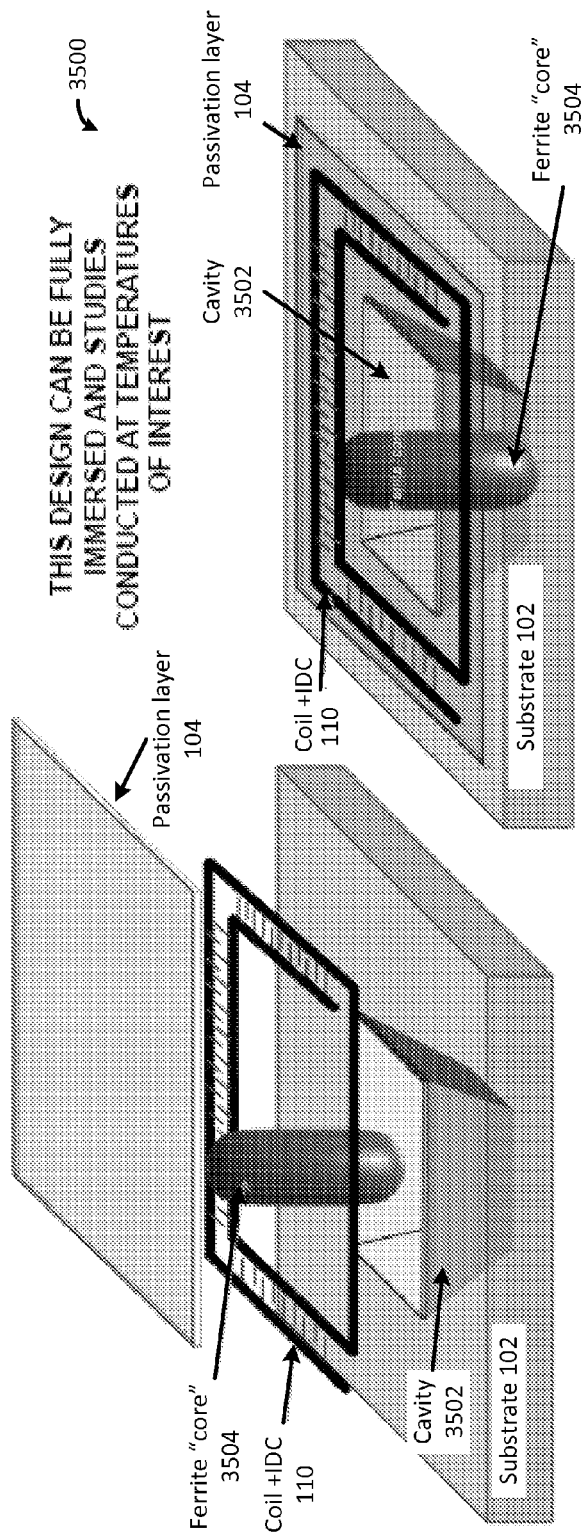
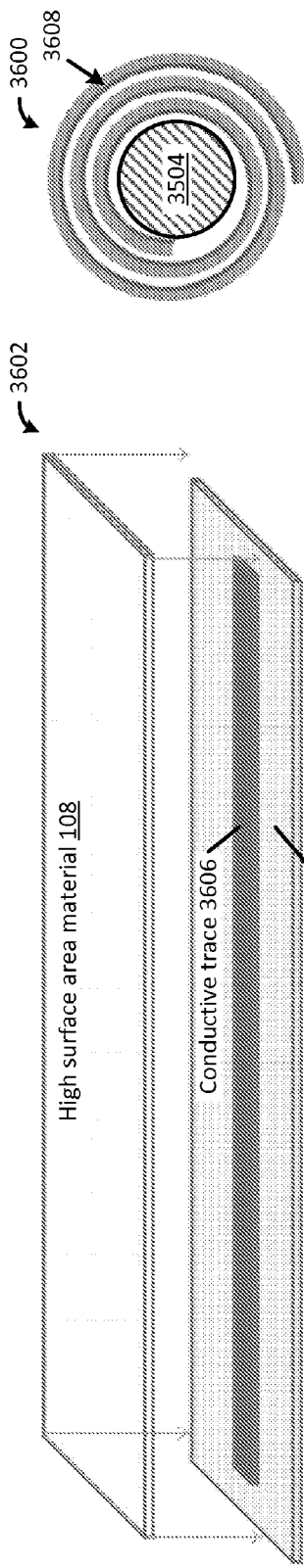
FIG. 35
FIG. 36A
FIG. 36B

Preliminary dielectric constant extraction

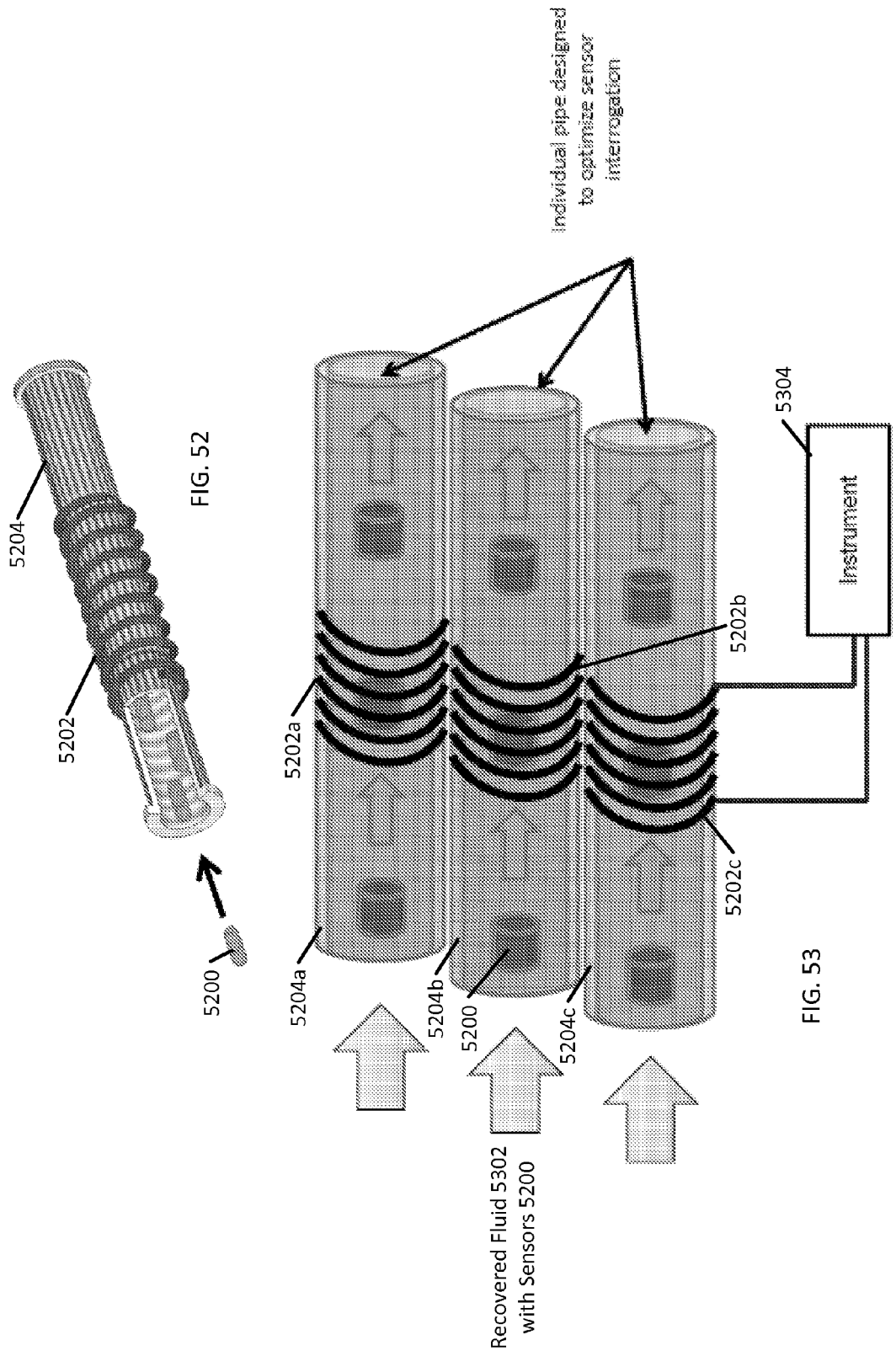

PASSIVE WIRELESS SELF-RESONANT SENSOR

CROSS-REFERENCE TO RELATED APPLICATIONS

This application is a National Stage patent application of and claims priority to International Application No. PCT/US2013/039604, filed May 5, 2013, which claims the benefit of U.S. Provisional Application No. 61/643,242 filed May 5, 2012, both of which are incorporated herein by reference in their entirety.

STATEMENT OF FEDERALLY FUNDED RESEARCH

Not Applicable.

THE NAMES OF THE PARTIES TO A JOINT RESEARCH AGREEMENT

Not Applicable.

INCORPORATION-BY-REFERENCE OF MATERIALS FILED ON COMPACT DISC

Not Applicable.

FIELD OF THE INVENTION

The present invention relates generally to the field of sensors and, more particularly, to a passive wireless self-resonant sensor.

BACKGROUND ART

Micromachined LC resonant sensors have design trade offs in size and sensitivity as well as size and coupling. Such sensors have to be carefully laid out to optimize sensitivity and read range. Meanwhile, a sensor's fabrication process needs to be low cost. Traditional sensor designs that connect separate inductor and capacitive transducer to form a LC resonant structure has two weaknesses: (1) the capacitor is put in the middle of the spiral inductor, reducing the coupling between sensor and reader; and (2) fabrication requires two photolithography steps.

Moreover, traditional coating techniques, such as spin coating, that utilize dissolution suffer from a lack of surface area resulting from the polymer filling gaps, rather than conforming to the surfaces. In addition, these traditional macroscopically thick coatings prevent or restrict capillary forces. As a result, their responsiveness to changes in liquid may the limited due to slow kinetic changes.

There is, therefore, a need for a self-resonant sensor that is more responsive to changes in a liquid, improves coupling between the sensor and reader, and is easier to fabricate.

SUMMARY OF THE INVENTION

The present invention provides a passive wireless self-resonant sensor having: (1) high responsiveness to changes in a liquid by conformal coating of a polymer on an open nanowire mat that allows the manipulation of surface properties within capillary-like voids to select what liquid may enter those voids and be sensed; (2) improved coupling between the sensor and reader by putting the capacitor in the interwinding area of the inductor; and (3) simplified fabrication because only one metal layer patterning step is required. The passive wireless self-resonant sensor can monitor both the dielectric constant and conductivity of target specific materials under test (e.g., chemical compounds, pH, hydrocarbons, fluids, gases, etc.), which are detected via changes in the resonance frequency and phase dip. Moreover, the passive wireless self-resonant sensor is disposable and can be used in high temperature environments.

One embodiment of the present invention provides a sensor for detecting one or more materials that includes a substrate, a passivation layer formed on the substrate, a self-resonant structure disposed in the passivation layer, and a high surface area material disposed on the passivation layer. The self-resonant structure includes a planar spiral inductor and a plurality of planar interdigitated capacitor electrodes disposed within the passivation layer. The planar spiral inductor includes an electrically conductive trace formed on the substrate in a planar spiral pattern having at least two turns and an inter-winding space between parallel segments of the electrically conductive trace. The plurality of planar interdigitated capacitor electrodes are electrically connected to the electrically conductive trace of the planar spiral inductor and formed on the substrate within the inter-winding space of at least one outermost turn of the planar spiral inductor. The high surface area material includes a conformal polymer coating to increase a sensitivity to the one or more materials.

Another embodiment of the present invention provides a sensor for detecting one or more materials that includes an elongated flexible substrate strip, a self-resonant structure disposed on elongated flexible substrate strip, and a high surface area material disposed on the elongated flexible substrate strip and an electrically conductive trace. The self-resonant structure includes the electrically conductive trace formed on the elongated flexible substrate proximate to a centerline of the elongated flexible substrate strip, the elongated flexible substrate strip rolled into a coil having a central void, and a ferrite core disposed within or through the central void of the coil. The high surface area material includes a conformal polymer coating to increase a sensitivity to the one or more materials.

Yet another embodiment of the present invention provides a sensor for detecting one or more materials that includes an elongated flexible substrate strip, a self-resonant structure and a high surface area material disposed on the elongated flexible substrate strip, a pair of electrically conductive traces and a plurality of planar interdigiated capacitor electrodes. The self-resonant structure includes the pair of electrically conductive traces formed on the elongated flexible substrate proximate to a centerline of the elongated flexible substrate strip such that the pair of electrically conductive traces are parallel to one another and separated by a gap, the plurality of planar interdigitated capacitor electrodes formed on the elongated flexible substrate, the elongated flexible substrate strip rolled into a coil having a central void, and a ferrite core disposed within or through the central void of the coil. The plurality of planar interdigitated capacitor electrodes are electrically connected to the pair of electrically conductive traces and formed on the elongated flexible substrate within the gap. The high surface area material includes a conformal polymer coating to increase a sensitivity to the one or more materials.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which:

FIGS. 5A-5E are block diagrams of a fabrication method for the self-resonant structure in accordance with one embodiment of the present invention;

FIG. 6 shows a self-resonant structure having 13 electrically conductive trace segments in accordance with one embodiment of the present invention;

FIGS. 14A-B are SEM images of free-standing films of pure germanium nanowires in accordance with one embodiment of the present invention;

FIG. 15 is an exploded diagram showing a current setup used in testing a sensor in accordance with the present invention;

FIG. 35 shows a sensor having a cavity and a ferrite core disposed within the sensor in accordance with yet another embodiment of the present invention.

FIGS. 36A-D show a "jelly roll" sensor for detecting one or more materials in accordance with yet another embodiment of the present invention;

FIG. 52 shows a reader in accordance with one embodiment of the present invention; and FIG. 53 shows a reader in accordance with another embodiment of the present invention.

DESCRIPTION OF THE INVENTION

Figure 1A:
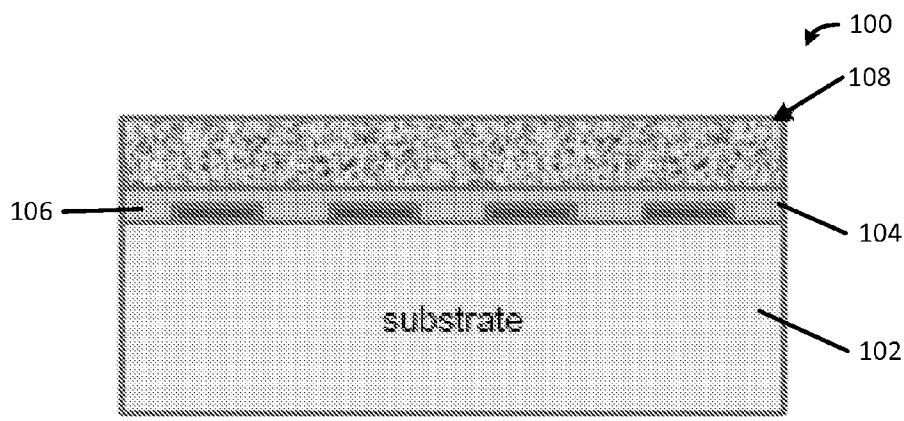
FIGS. 1A and 1B are block diagrams of a sensor for detecting one or more materials in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to chemical sensors and electronics, but it will be understood that the concepts of the present invention are applicable to any self-resonant sensor.

The present invention provides a wireless self-resonant sensor having: (1) high responsiveness to changes in a liquid by conformal coating of a polymer on a high surface area material, such as an open nanowire mat, that allows the manipulation of surface properties within capillary-like voids to select what liquid may enter those voids and be sensed; (2) improved coupling between the sensor and reader by putting the capacitor in the interwinding area of the inductor; and (3) simplified fabrication because only one metal layer patterning step is required. The surface properties of the high surface area material can be controlled to determine which liquids have sufficient affinity to be pulled into the internal void space. Because of the sensor's planar structure, chemically sensitive coatings could be easily integrated with the sensor. The passive wireless self-resonant sensor can monitor both the dielectric constant and conductivity of target specific materials under test (e.g., chemical compounds, pH, hydrocarbons, fluids, gases, etc.), which are detected via changes in the resonance frequency and phase dip. Moreover, the passive wireless self-resonant sensor is disposable and can be used in high temperature environments.

Applications of the present invention may include, but are not limited to, non-destructive evaluation, liquid/gas material monitoring, minority component detection, discrimination/detection of a change in the liquid pH, salinity, organic content, hydrophilic nature, hydrophobic nature.

One embodiment of the present invention is designed and fabricated using a microfabricated inductor with interdigitated capacitors (IDC). A self-resonant-structure (SRS) is designed by incorporating IDC electrodes in the inter-winding space of the inductor. The distributed capacitance and conductance of the sensor is affected by dielectric constant ($\in$) and conductivity ($\sigma\sigma$) of its environment or material under test (MUT). The $\in$ and $\sigma$ can be used to provide information about the surrounding environment. This serves as an impedance transducer changing the resonant frequency and phase dip of the SRS.

To increase the sensitivity of the sensor, a layer of semiconductor nanowires is placed on top of the SRS in the form of a nonwoven nanowire mat, or fabric. This nanowire mat provides a low-cost, high surface-area scaffold which can be tailored to introduce chemical specificity to the sensor. The nanowire mats consist of silicon (Si) or germanium (Ge) nanowires, which can be synthesized in macroscopic quantities and at low cost using a supercritical fluid-liquid-solid (SFLS) growth process. Si and Ge nanowires are grown in supercritical toluene using liquid-phase precursors (e.g. diphenylgermane, monophenylsilane, trisilane) and colloidal gold nanocrystal seeds. The nanowires are single-crystalline, with average diameters ranging from 25 to 50 nm and lengths ranging from 10s to 100s of micrometers. As synthesized, the nanowires have hydrophobic surfaces. These surfaces can be modified via covalent and non-covalent methods to change the material from hydrophobic to hydrophilic, or to introduce chemical functionality. The nanowires are formed into mats by dispensing dispersions of semiconductor nanowires into a Teflon trough, allowing the solvent to evaporate, and then removing the nanowire mat from the Teflon substrate. The nanowire mats retain the chemical characteristics and functionality of the nanowires, and can be cut to fit the desired sensor geometry. The nanowire mats are highly porous with roughly 90% void space, allowing for high analyte penetration, and strong capillary forces which aid in drawing analyte towards the SRS in a liquid environment.

A polymer coating is added to the nanowire mat to control the surface properties as desired. To achieve a conformal coating and take advantage of the high surface area of the nanowire mat, a coating is grown in vacuum directly from the vapor phase via initiated chemical vapor deposition (iCVD). This system yields a polymer coating ranging from 10 nm-3 µm, with a typical targeted value in the tens of nanometers. The chemistry is important by both allowing selective dissolution of the polymer in the sensor's target environment, where the liquid phase will replace the volume occupied by the polymer (i.e. aliphatic hydrocarbons dissolving poly [hexyl methacrylate]), and by controlling the surface properties of the nanowires to entrain a compatible liquid into the void space (i.e. uncoated nanowire mats drawing hydrocarbons in the voids, whereas poly[acrylic acid] draw in water). Both targeted dissolution and drawing in a target liquid provide a change in $\in$ that can be measured.

The SRS is interrogated using a non-contact inductively coupled reader coil. The change in resonance frequency and phase dip of the SRS is used to detect material properties of the environment/MUT. Sensor layout is optimized based on the relationship between sensor layout and coupling factor between sensor and reader. The sensor's response to variety of liquid MUTs with a wide range of dielectric constant and conductivity is verified in measurements.

Figure 1B:
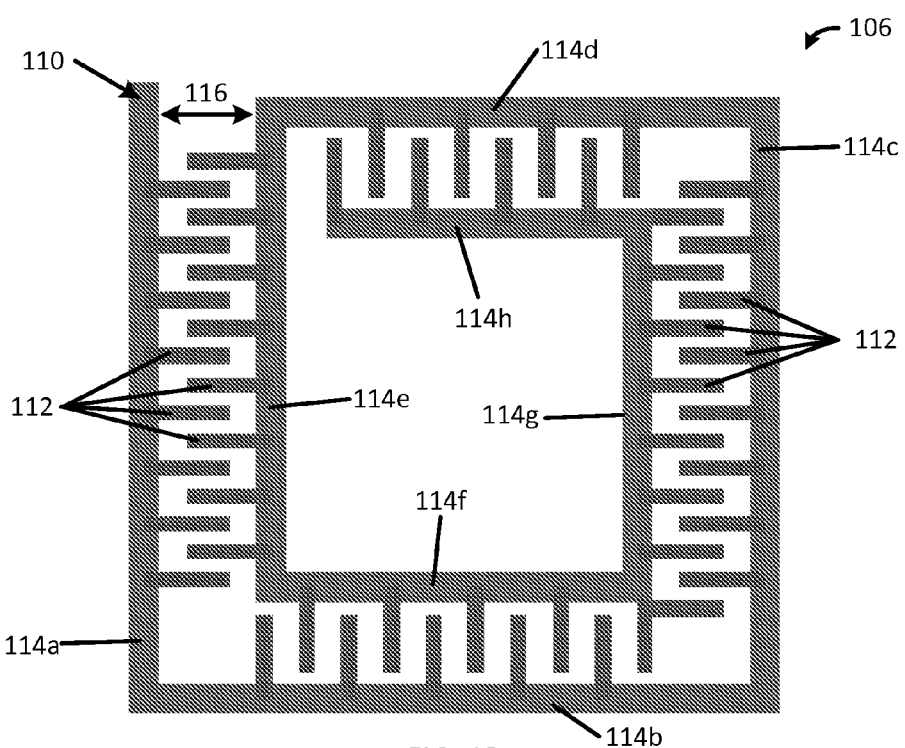

Now referring to FIGS. 1A and 1B, block diagrams of a sensor 100 for detecting one or more materials is shown. The sensor 100 includes a substrate 102, a passivation layer 104 formed on the substrate 102, a self-resonant structure 106 disposed in the passivation layer 104, and a high surface area material 108 disposed on the passivation layer 104. The self-resonant structure 106 includes a planar spiral inductor 110 and a plurality of planar interdigitated capacitor (IDC) electrodes 112 disposed within the passivation layer 104. The planar spiral inductor 110 includes an electrically conductive trace 114 formed on the substrate 102 in a planar spiral pattern having at least two turns and an inter-winding space 116 between parallel segments of the electrically conductive trace. The plurality of planar interdigitated capacitor electrodes 112 are electrically connected to the electrically conductive trace 114 of the planar spiral inductor 110 and formed on the substrate 102 within the inter-winding space 116 of at least one outermost turn of the planar spiral inductor 110. The number of turns can correspond to the number of "sides" or conductive trace segments or the number of inductor "winding" turns. For example, the first inductor winding turn of the planar spiral inductor 110 includes electrically conductive trace segments (or turns or sides) 114a, 114b, 114c and 114d, and the second inductor winding turn includes electrically conductive trace segments (or turns or sides) 114e, 114f, 114g and 114h. As will be described in more detail below, the high surface area material 108 (e.g., a nonwoven nanowire mat or fabric of silicon or germanium nanowires) includes a conformal polymer coating to increase sensitivity to the one or more materials (e.g., chemical compounds, pH, hydrocarbons, fluids, gases, etc.). A dielectric constant and a conductivity of the one or more materials in contact with the self-resonant structure affect a capacitance and a conductance of the self-resonant structure causing a change in a resonant frequency and a phase dip of the self-resonant structure. The change in the resonant frequency and the phase dip of the self-resonant structure is detected using a non-contact inductively coupled reader coil.

Figure 2:
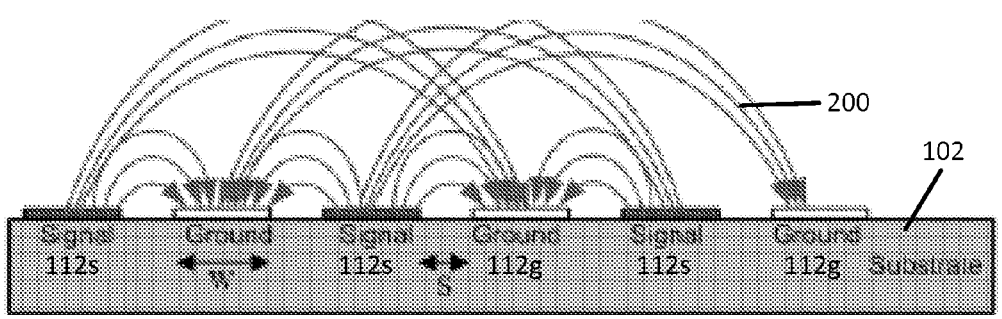
FIG. 2 is a diagram showing the interdigitated, finger-like electrodes are used as two terminals of the capacitor in accordance with one embodiment of the present invention.

As shown in FIG. 2, the interdigitated, finger-like electrodes 112 are used as two terminals of the capacitor. The electric field 200 originates from one group of signal electrodes 112s, coming up and penetrating into the MUT, then terminating at another group of ground electrodes 112g. The length of the electrodes 112 and number of electrode pairs is directly proportional to total capacitance. Changing the sum of width (W) and spacing (S) of electrodes 112 does not change total capacitance. The sensor's range is determined by how far the fringing electric field can penetrate into the material under test. Using a finite-element simulation, it is found that the range is 1.5 times the sum of W and S. In order to increase the coupling between the reader and the sensor tag, there should not be large continuous metal sheet in the interior area of spiral inductor, the area where most magnetic flux will come through. The large metal piece in this area will produce eddy current, which will compromise the coupling factor and shift resonant frequency. Placing the IDC in the middle part is not the most efficient way of laying out the sensor. When sum of spiral inductor's width and spacing is fixed, changing the ratio between them does not change the mutual inductance between reader and the tag. The inductor width/spacing ratio can be increased to improve coupling of spiral inter-windings and reduces the total area of the spiral[2].

Figure 3:
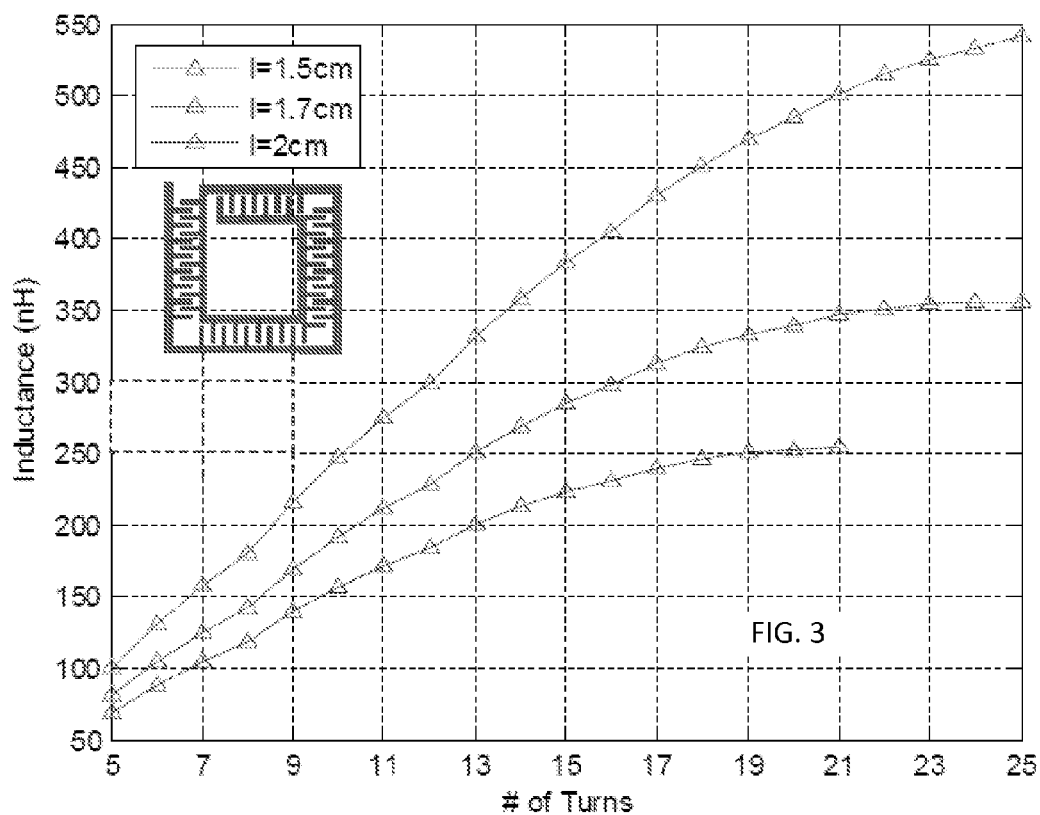
FIG. 3 is a graph of the inductance vs. the number of turns or sides to the self-resonant structure in accordance with one embodiment of the present invention.
Figure 4:
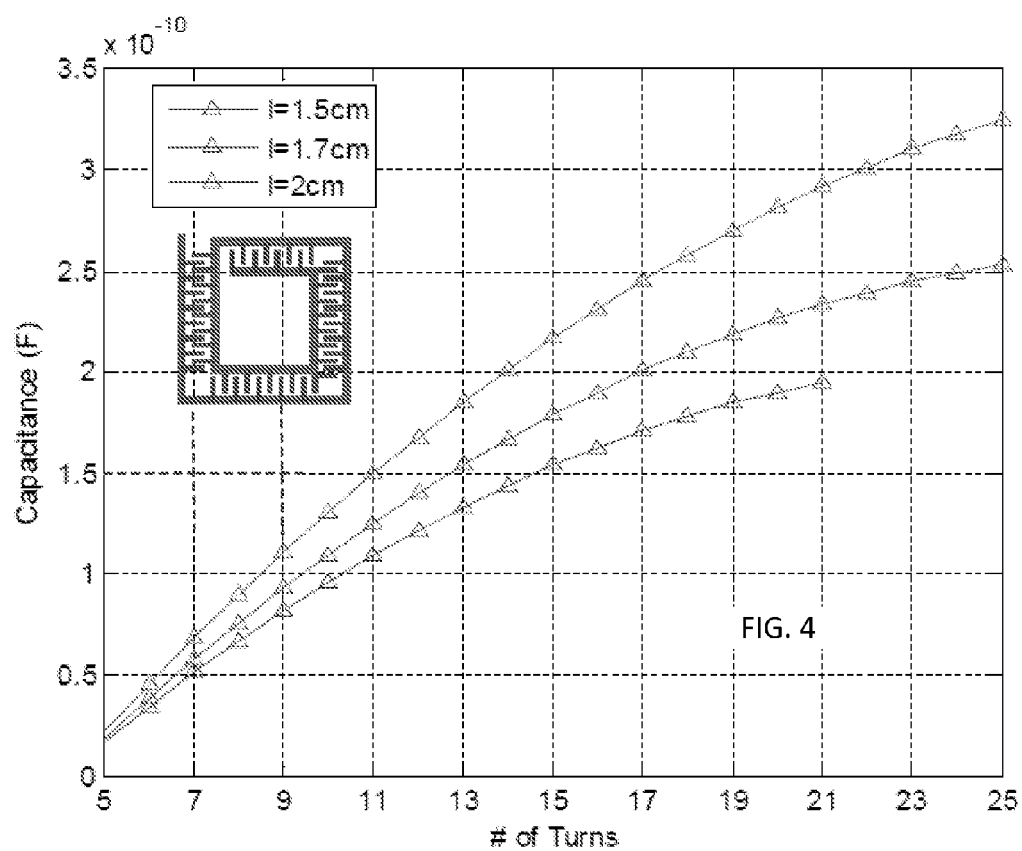
FIG. 4 is a graph of the capacitance vs. the number of turns or sides to the self-resonant structure in accordance with one embodiment of the present invention.

Note that the planar spiral pattern of the present invention is not limited to the examples shown in the figures. The planar spiral pattern can be a spiral circle pattern, a spiral oval pattern, a spiral elliptical pattern, a spiral triangular pattern, a spiral square pattern, a spiral rectangular pattern, a spiral pentagon pattern, a spiral octagon pattern, a spiral hexagon pattern, a spiral polygon pattern or a combination thereof. Integrating the inductor and the capacitor into one integrated structure provides the simplest possible construction that allows the smallest over-all chip size using monolithic fabrication with no discrete components. This platform allows any deposition process to be used to coat the high surface area material 108 or the sensor 100. FIG. 3 is a graph of the inductance vs. the number of turns or sides to the self-resonant structure 106. FIG. 4 is a graph of the capacitance vs. the number of turns or sides to the self-resonant structure 106. In FIGS. 3 and 4, the "number of turns" corresponds to the number of "sides". In the example shown in the inset, there are 8 "turns".

Referring now to FIGS. 5A-5E, a method 500 for fabricating the self-resonant structure 106 is shown. A substrate (e.g., quartz, polyimide (flexible) or other suitable material) 102 is provided in FIG. 5A. A photoresist and LOR resist 502 are formed on the substrate 102 in a negative pattern of the self-resonant structure 106 using negative photolithography or other suitable techniques in FIG. 5B. E-beam evaporation of a Cr/Au seed layer 504 is shown in FIG. 5C. A lift-off process to pattern the metal layer 504 forming the electrically conductive traces 114 is shown in FIG. 5D. Gold or other suitable metal is then electroplated on the metal layer as shown in FIG. 5E. The insulation or passivation layer 104 (not shown) is then added using suitable techniques.

Figure 7:
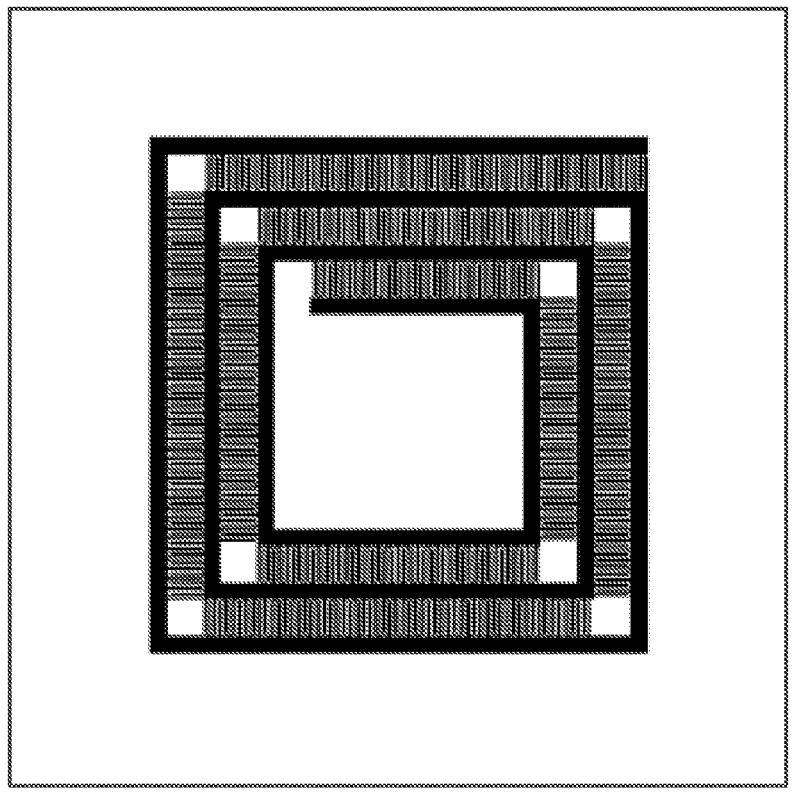
FIG. 7 shows a self-resonant structure having 17 electrically conductive trace segments in accordance with one embodiment of the present invention.
Figure 8:
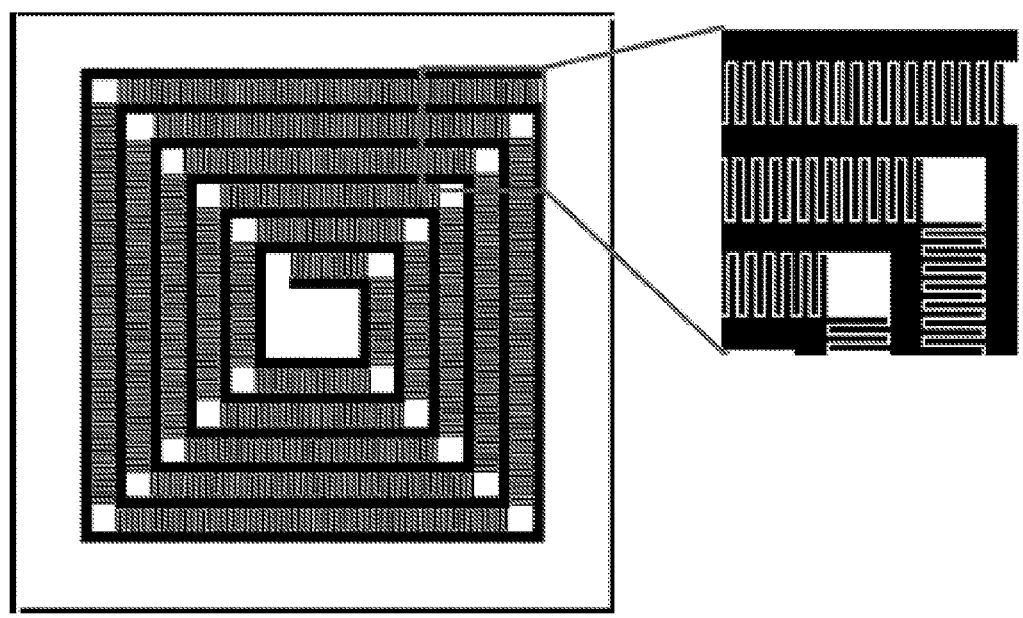
FIG. 8 shows a self-resonant structure having 25 electrically conductive trace segments in accordance with one embodiment of the present invention.

FIG. 6 shows a self-resonant structure having 13 electrically conductive trace segments, 1.4 cm outer trace dimension, 0.6 cm interior trace dimension, 500 μm inductor width, 1000 μm inductor spacing, 30 MHz estimated resonant frequency, 100 IDC finger width and 400 IDC finger spacing. FIG. 7 shows a self-resonant structure having 17 electrically conductive trace segments, 1.7 cm outer trace dimension, 0.6 cm interior trace dimension, 500 μm inductor width, 1000 μm inductor spacing, 20 MHz estimated resonant frequency, 100 IDC finger width and 400 IDC finger spacing. FIG. 8 shows a self-resonant structure having 25 electrically conductive trace segments, 2 cm outer trace dimension, 0.3 cm interior trace dimension, 500 μm inductor width, 1000 μm inductor spacing, 12 MHz estimated resonant frequency, 100 IDC finger width and 400 IDC finger spacing.

Figure 9A:
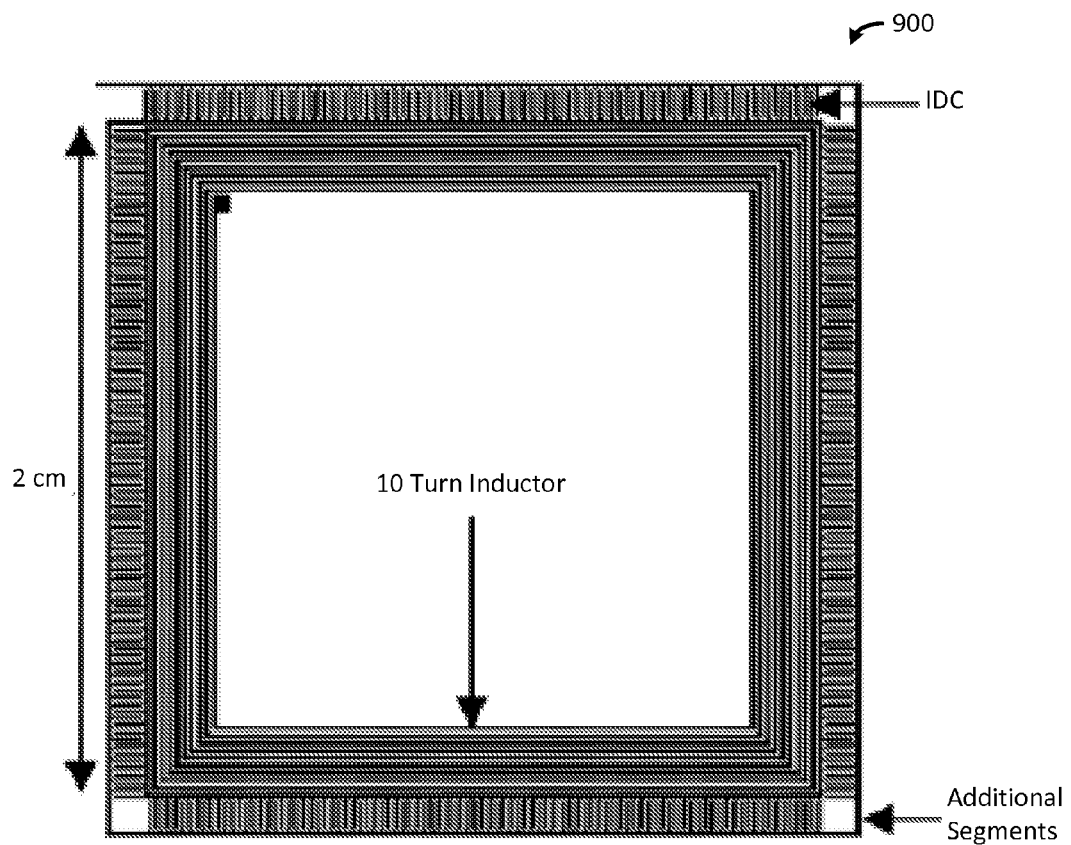
FIGS. 9A-C show a self-resonant structure with the interdigitated capacitor electrodes only located in the inter-winding space of the outermost turn of the planar spiral inductor in accordance with another embodiment of the present invention.
Figure 9B:
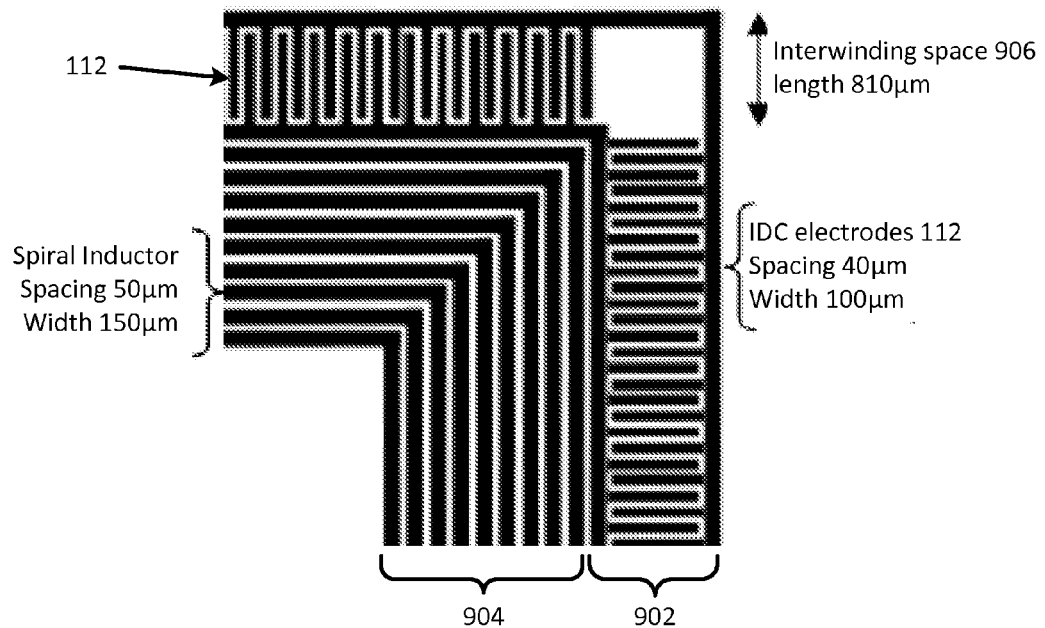
Figure 9C:
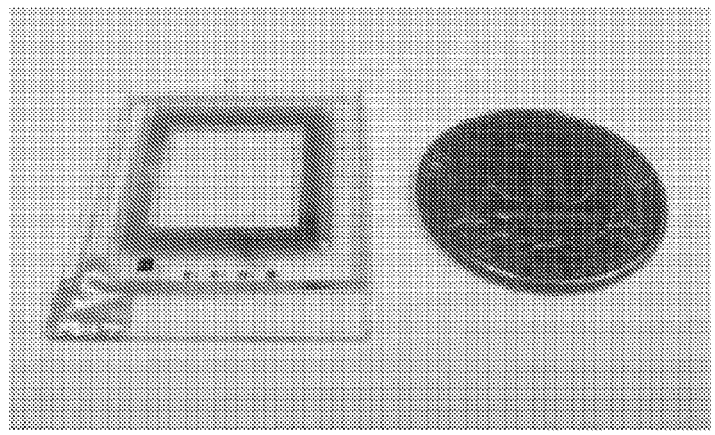
Figure 10A:
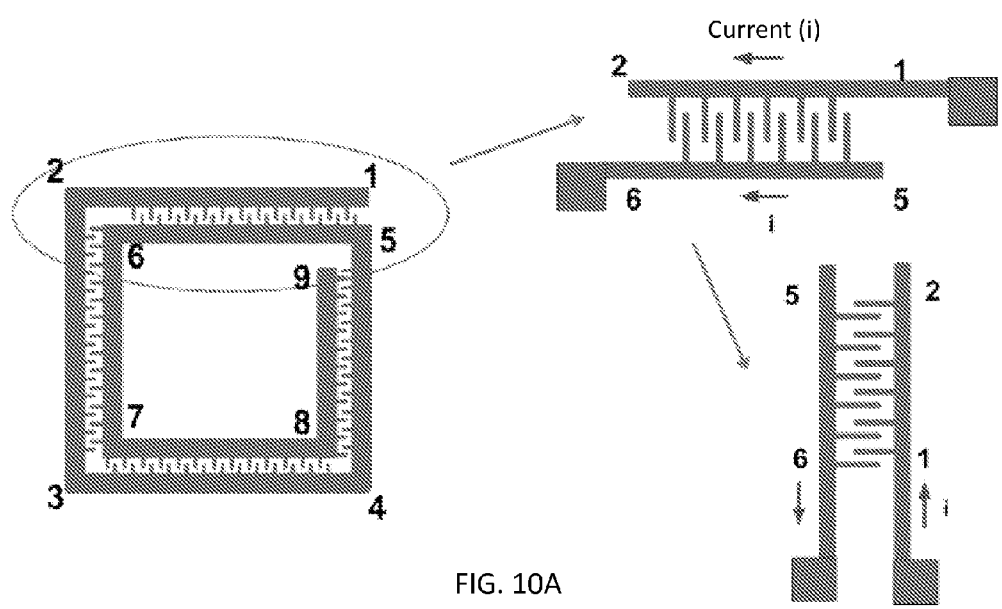
FIGS. 10A-C are diagrams showing how the self-resonant structure can be modeled in accordance with one embodiment of the present invention.
Figure 10B:
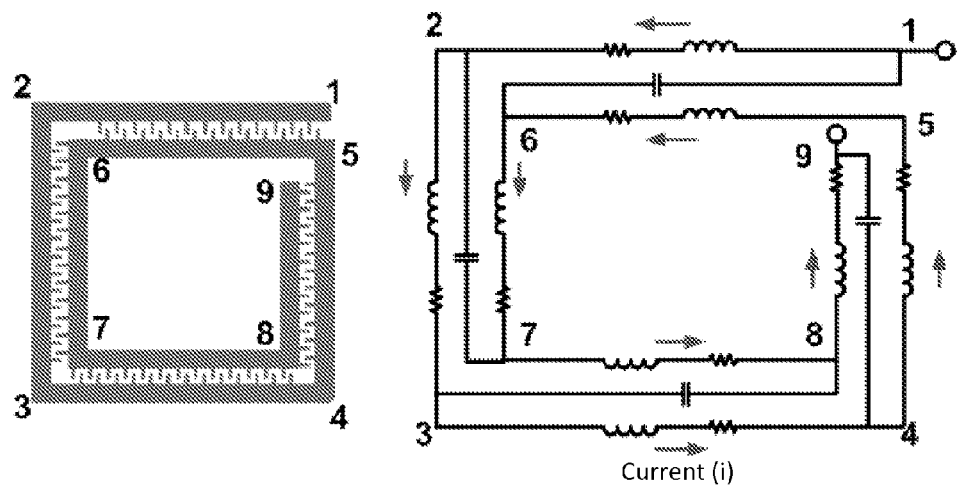
Figure 10C:
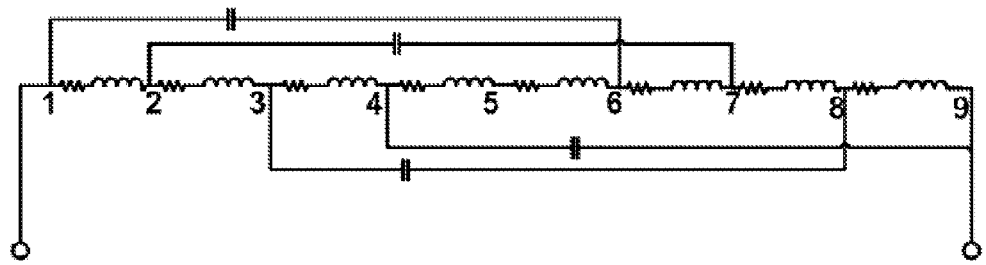
Figure 11:
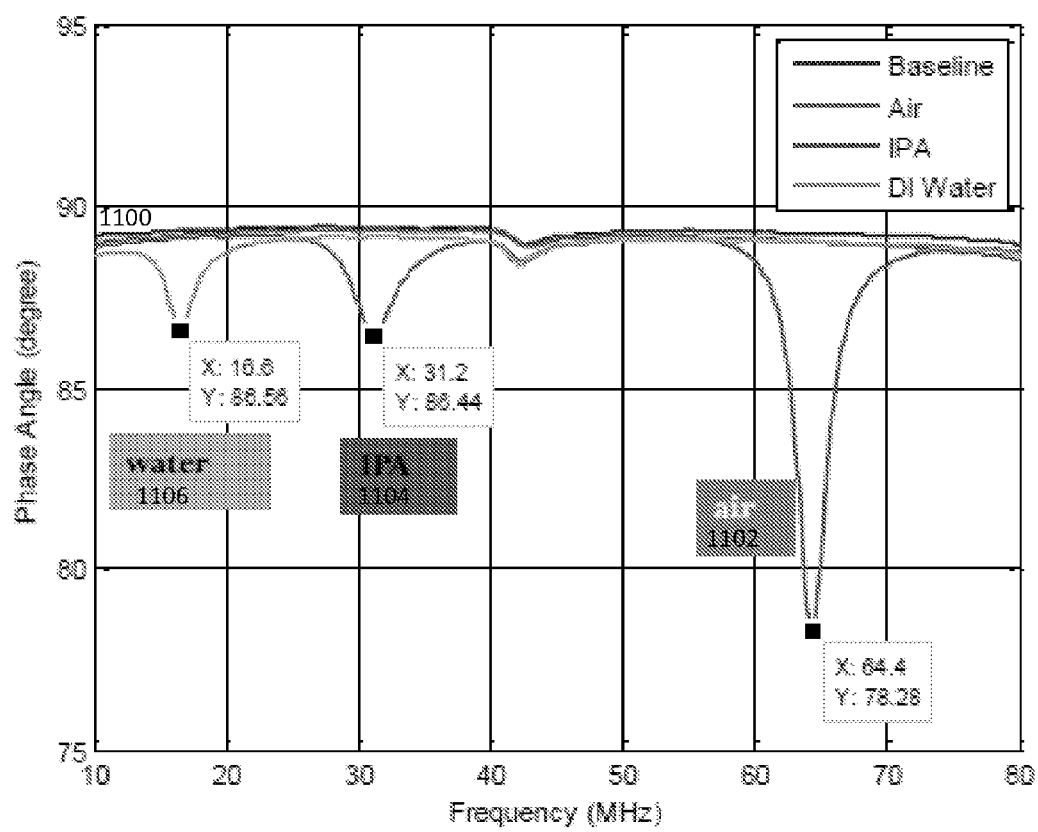
FIG. 11 is a graph showing measurements of phase angle vs. frequency of the self-resonant structure of FIGS. 8A-C in contact with various materials in accordance with one embodiment of the present invention.

Referring now to FIGS. 9A-C, a self-resonant structure 900 having 11 inductor winding turns (one outer winding turn 902 plus 10 inner winding turns 904), 2 cm outer trace dimension, 1 cm inner trace dimension, 850 μm inter-winding space length, 150 μm inductor width, 50 μm inductor spacing, 100 μm IDC finger width and 40 μm IDC finger spacing is shown. The interdigitated capacitor electrodes 112 are only located in the inter-winding space 906 of the outermost turn 902 of the planar spiral inductor. The self-resonant structure 900 can be modeled as shown in FIGS. 10A-C. A graph shown measurements of phase angle vs. frequency of the self-resonant structure 900 of FIGS. 9A-C in contact with various materials (baseline 1100 "blue" line, air 1102 "green" line, IPA 1104 "red" line, DI water 1106 "turquoise" line) is shown in FIG. 11. The resonance near 40 MHz is from the cable and reader.

| Material under test | Relative dielectric constant | Measured resonant frequency (MHz) | Phase dip (degrees) |
| --- | --- | --- | --- |
| Air 1102 | 1 | 64.4 | 10.8 |
| IPA 1104 | 18 | 31.2 | 2.7 |
| DI-water 1106 | 80 | 16.6 | 2.1 |

Figure 12:
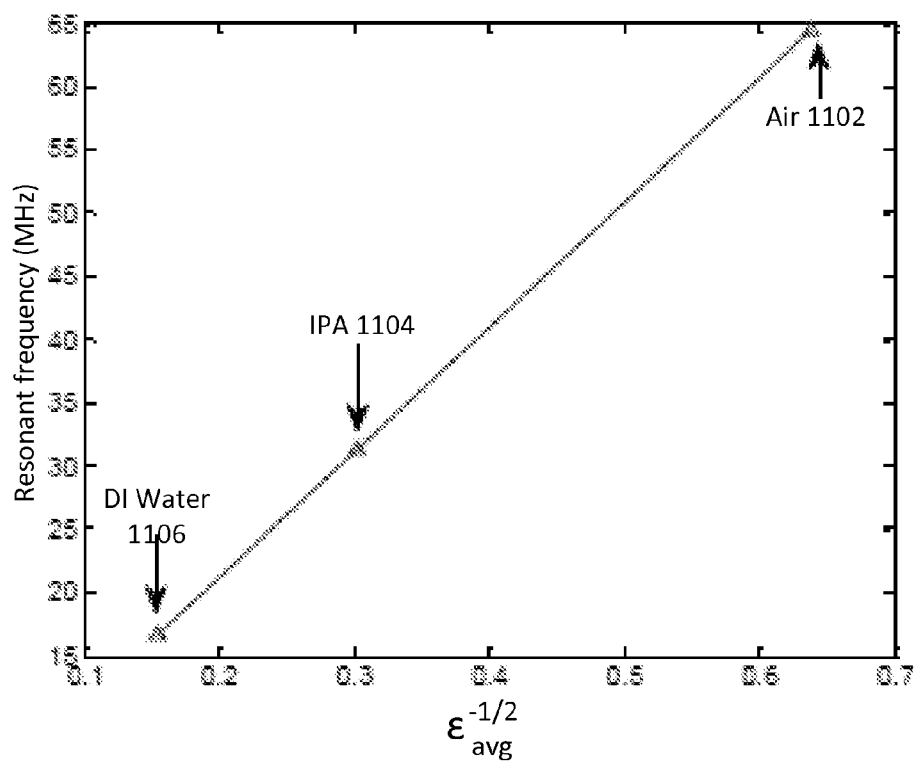
FIG. 12 is graph showing the resonant frequency is proportional to inverse of the square root of average dielectric constant in accordance with the present invention.

As shown in FIG. 12, the resonant frequency is proportional to inverse of the square root of average dielectric constant:

$$f_0 = \frac{1}{2\pi\sqrt{LC}} \alpha \frac{1}{\sqrt{C}} \alpha \frac{1}{\sqrt{\varepsilon_{avg}}} \text{ where } \varepsilon_{avg} = (\varepsilon_{MUT} + \varepsilon_{SiO2})/2.$$

Figure 13A:
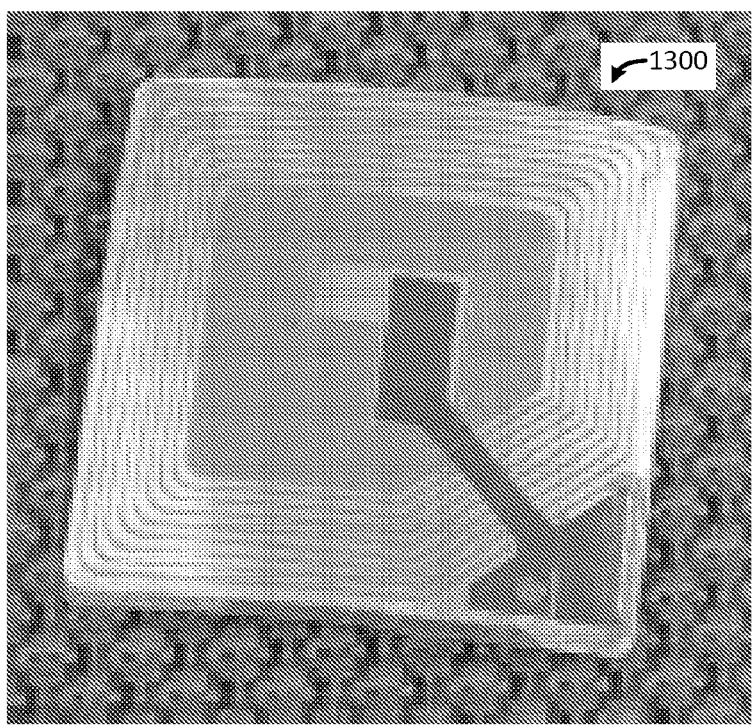
FIG. 13A shows a commercially available EAS tag in accordance with the prior art.
Figure 13B:
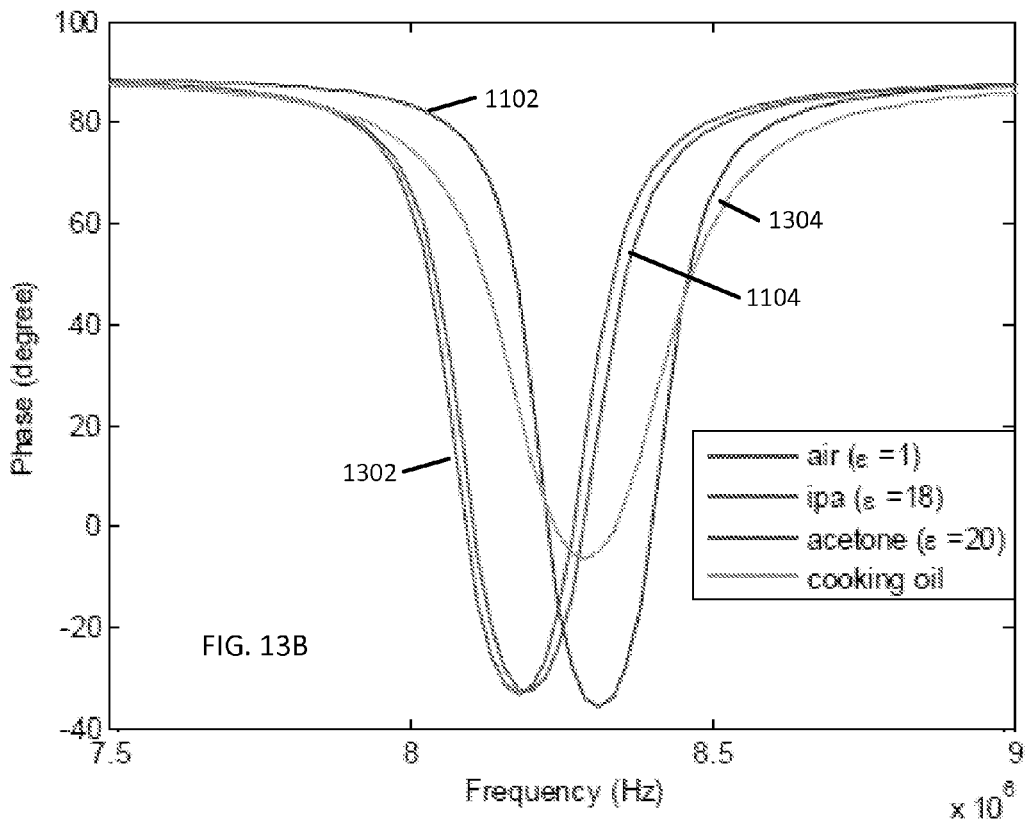
FIGS. 13B-13E are graphs showing measurements of phase angle vs. frequency of the EAS tag of FIG. 13A in contact with various materials.
Figure 13C:
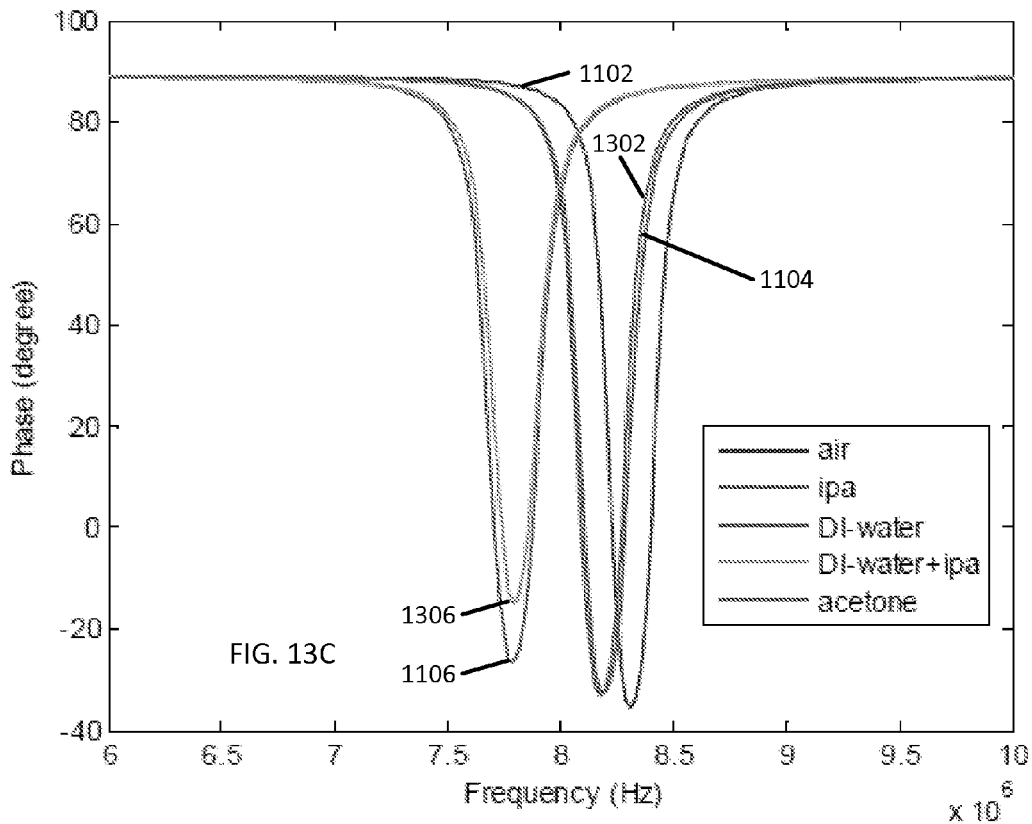
Figure 13D:
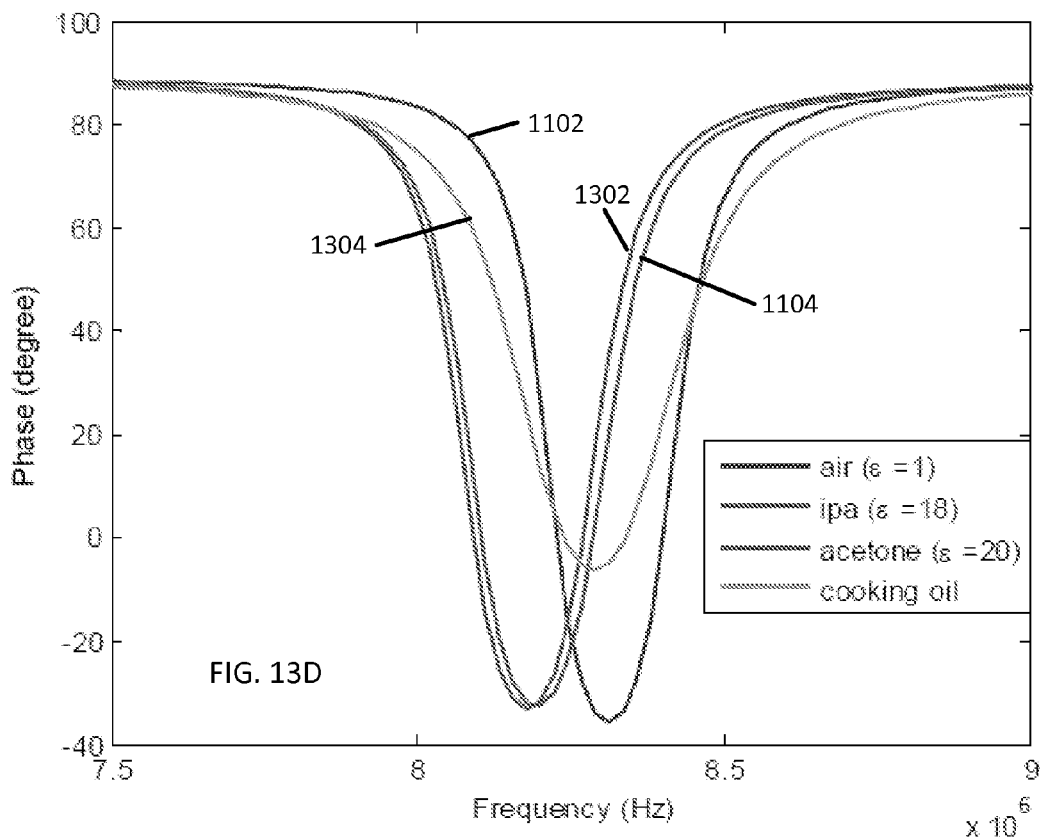
Figure 13E:
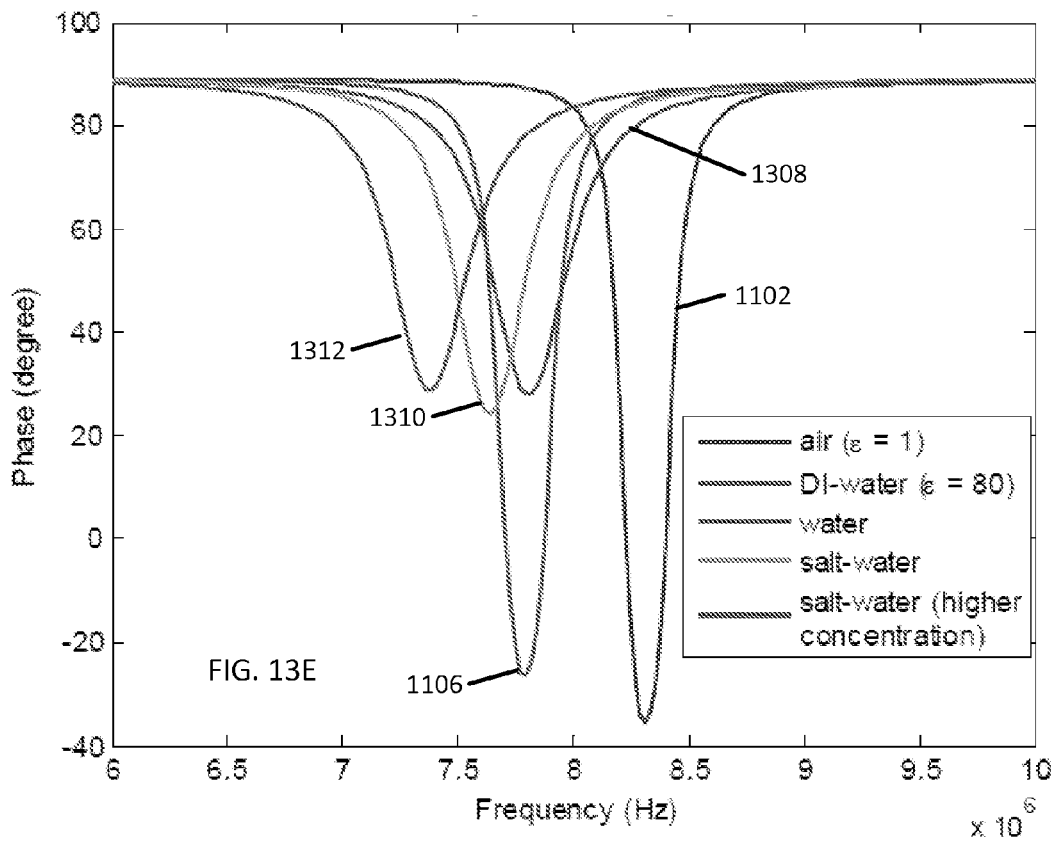

In contrast, measurements of phase angle vs. frequency of a commercially available EAS tag 1300 (FIG. 13A) in contact with various materials (air 1102, IPA 1104, DI water 1106, acetone 1302, cooking oil 1304, DI water+IPA 1306, tap water 1308, salt water 1310, salt water (higher concentration) 1312) are shown in FIGS. 13B-13E. The changes are induces by the change in inter-turn capacitance. The EAS tags 1300 have an internal fixed capacitor. The summary of the results are:

| Fluid | $f_0$ (MHz) | pseudoQ | Capacitance Change |
|---|---|---|---|
| IPA 1104 | 7.75 | 37.8 | 2.4% |
| Acetone 1302 | 7.75 | 38.9 | 2.4% |
| Oil 1304 | 8.25 | 30.0 | 0.7% |
| DI water 1106 | 7.75 | 35.4 | 15% |
| tap water 1308 | 7.75 | 20.4 | 15% |
| salt water (1) 1310 | 7.6 | 21.9 | 19% |
| salt water (2) 1312 | 7.3 | 20.9 | 29% |

As previously mentioned, the high surface area material 108 can be a nonwoven nanowire mat or fabric of silicon or germanium nanowires and typically has about 90% void space that allows high analyte penetration and strong capillary forces. The silicon nanowires used in some of the sensor tests has a thickness ranging from 25-75 μm and 1 cm$^2$ has roughly 450 cm$^2$ of surface area. The silicon or germanium nanowires are single-crystalline having a hydrophobic surface, an average diameter ranging from about 25 to 50 nm and an average length ranging from about 10 to 500 mm. Note that a covalent or non-covalent process can be used to change the hydrophobic surface to a hydrophilic surface or provide a specified chemical functionality.

The silicon or germanium nanowires can be made using a supercritical fluid-liquid-solid growth process: (1) dispensing dispersions of the silicon or germanium nanowires into a Teflon trough containing a solvent; (2) allowing the solvent to evaporate; and (3) removing the resulting nonwoven nanowire mat or fabric from the Teflon trough. The solvent can be supercritical toluene with one or more liquid-phase precursors (e.g., diphenylgermane, monophenylsilane, trisilane, etc.) and a plurality of colloidal gold nanocrystal seeds. For example: (1) silicon nanowire can be grown using trisilane (TS) as the reactant with a thin (≈2 nm) layer of oxide on the surface; (2) silicon nanowire can be grown using monophenylsilane (MPS) as the reactant with a thin (3-4 nm) shell of polyphenylsilane on the surface; and (3) germanium nanowire can be grown using diphenylgermane (DPG) as the reactant. One or more surface properties of the high surface area material 108 are selected to draw the one or more materials into the self-resonant structure 106. FIGS. 14A-B are SEM images of free-standing films of pure germanium nanowires.

The conformal polymer coating on the high surface area material can be applied in vacuum directly from a vapor phase via initiated chemical vapor deposition (iCVD) or other techniques. The iCVD process has several advantages over a solution polymerization process: (1) conformal coating of 3-D surfaces; (2) nanometer scale thickness control; and (3) no solvent is required. The iCVD process utilizes an initiator and at least one monomer to polymerize from vapor phase. A heated filament (~200° C.) cracks initiator. The monomer concentration is delivered from vapor according to adsorption isotherm. The initiator starts polymerization of the monomers absorbed on the target surface. Pressures are approximately 0.5 to 1 torr during operation. Some examples of conformal polymer coatings include a hexyl acrylate monomer, a benzyl methacrylate monomer, or an ethylene glycol diacrylate monomer. It is possible options to mix 2 different monomers or a monomer+crosslinker. For example, a methacrylic acid (monomer) with a tertiary butyl peroxide (initiator) yields a poly-methacrylic acid (polymer). Poly-methacrylic acid is soluble in water and can be crosslinked, such that the crosslinked poly-methacrylic acid would swell in the presence of water. This dissolution or swelling can be detected by the sensor. In another example, a 4-vinylpyridine (monomer) with a di-tert-butyl peroxide (initiator) yields a poly 4-vinylpyridine (polymer).

An initial setup used liquid injectors to deliver small doses of both initiator and monomer into He carrier gas streams. This was incompatible with the monomer and it reacted within the injector body. As a result, current setups use liquid injectors to deliver the initiator, but use a bubbler to deliver the monomer. A 4:1 monomer to initiator ratio provides 5 to 50 nm films on planar substrates (by ellipsometry). A thickness of around 5 nm to 3 μm is desirable, but not required, to preserve high surface area and give enough volume to detect changes.

Figure 16A:
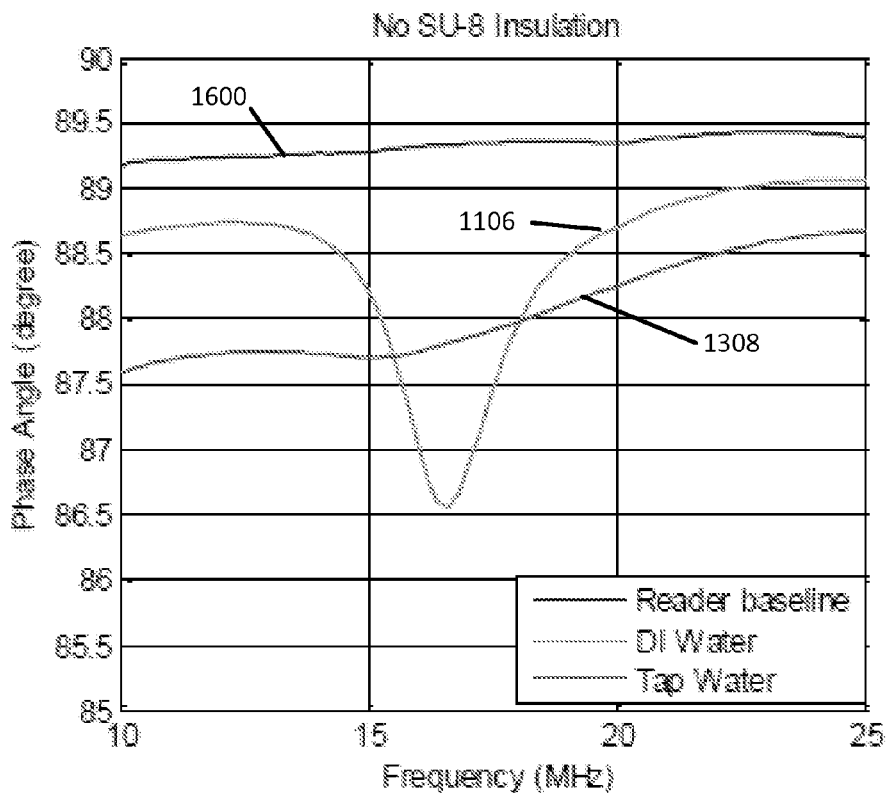
FIGS. 16A-B are graphs showing measurements for the sensor with and without the SU-8 insulation layer in accordance with the present invention.
Figure 16B:
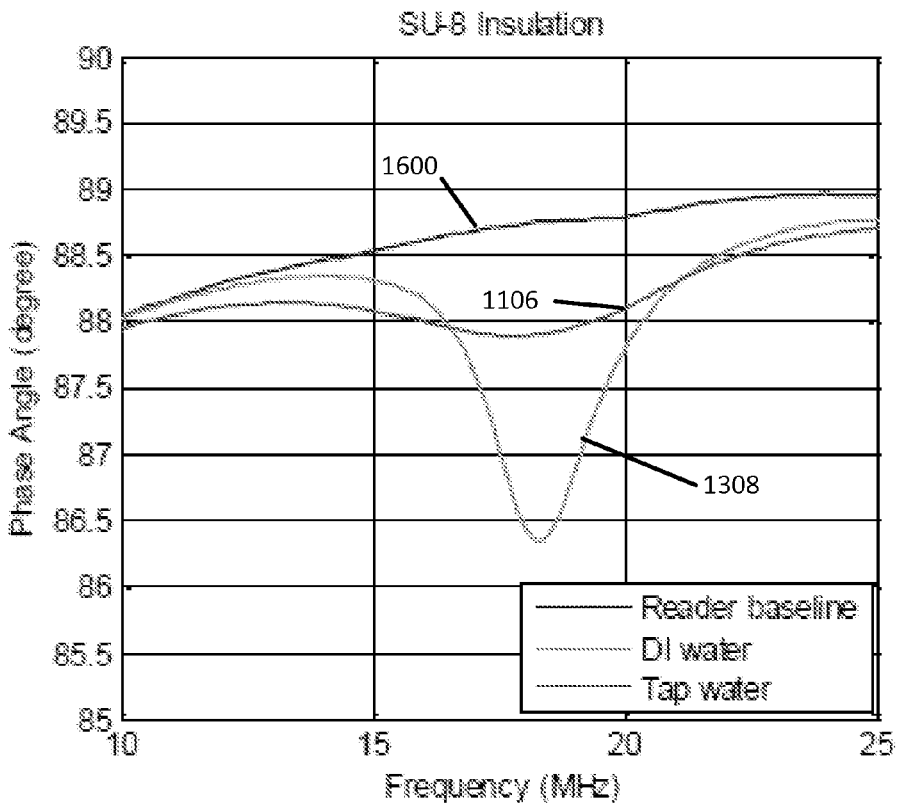
Figure 17:
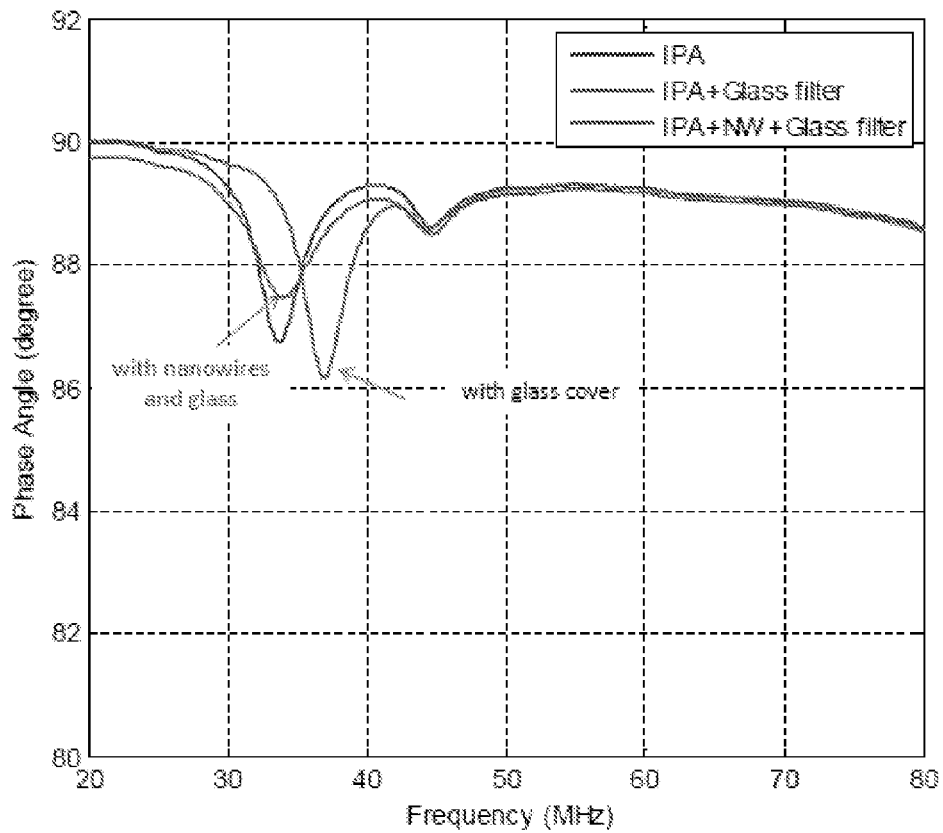
FIG. 17 is a graph showing the resonant frequency and phase angle dip of various cover layers on the sensor in accordance with one embodiment of the present invention in the presence of a solvent of isopropanol alcohol.
Figure 18:
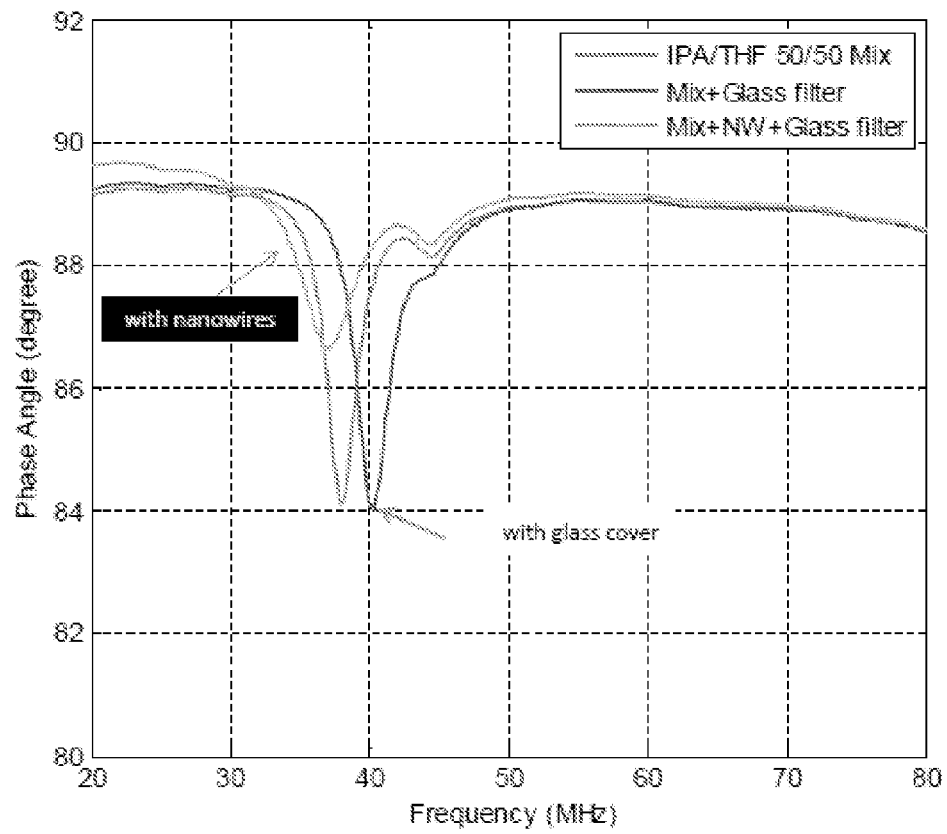
FIG. 18 is a graph showing the resonant frequency and phase angle dip of various cover layers on the sensor in accordance with one embodiment of the present invention in the presence of solvent mix of 50% isopropanol alcohol and 50% hexane.
Figure 19:
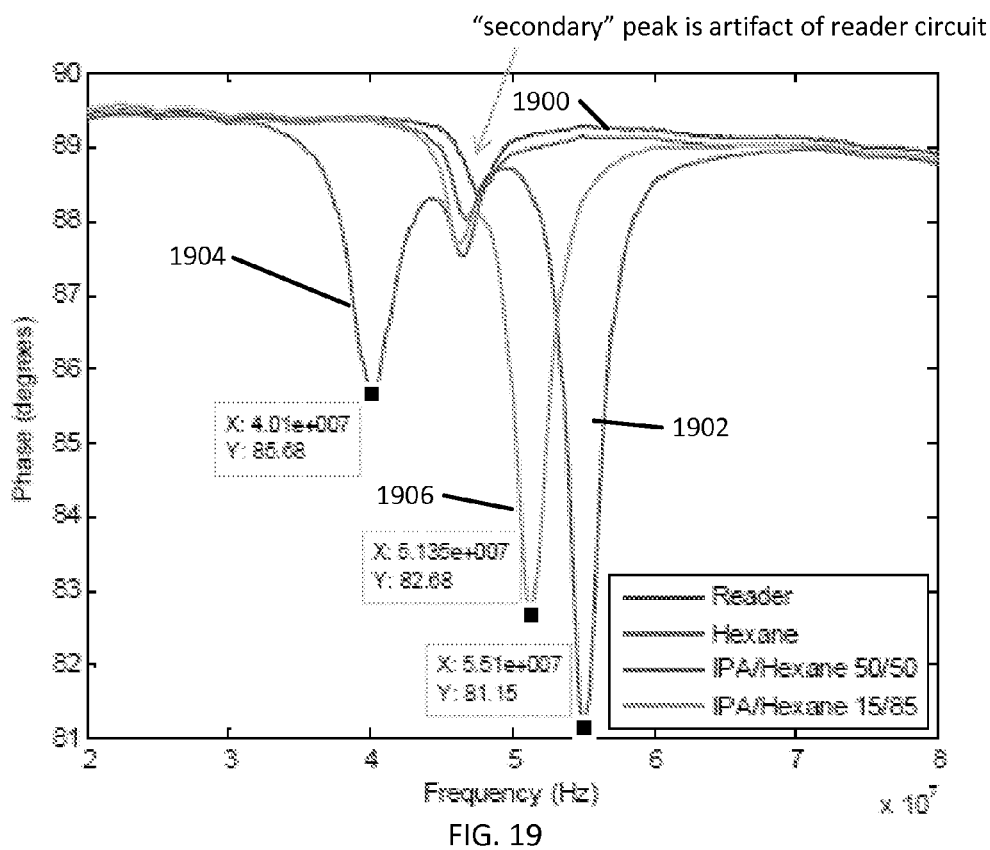
FIG. 19 is a graph showing the resonant frequency and phase angle dip of the sensor in accordance with one embodiment of the present invention plus porous glass without the nanowire fabric in the presence of various solvents.
Figure 20:
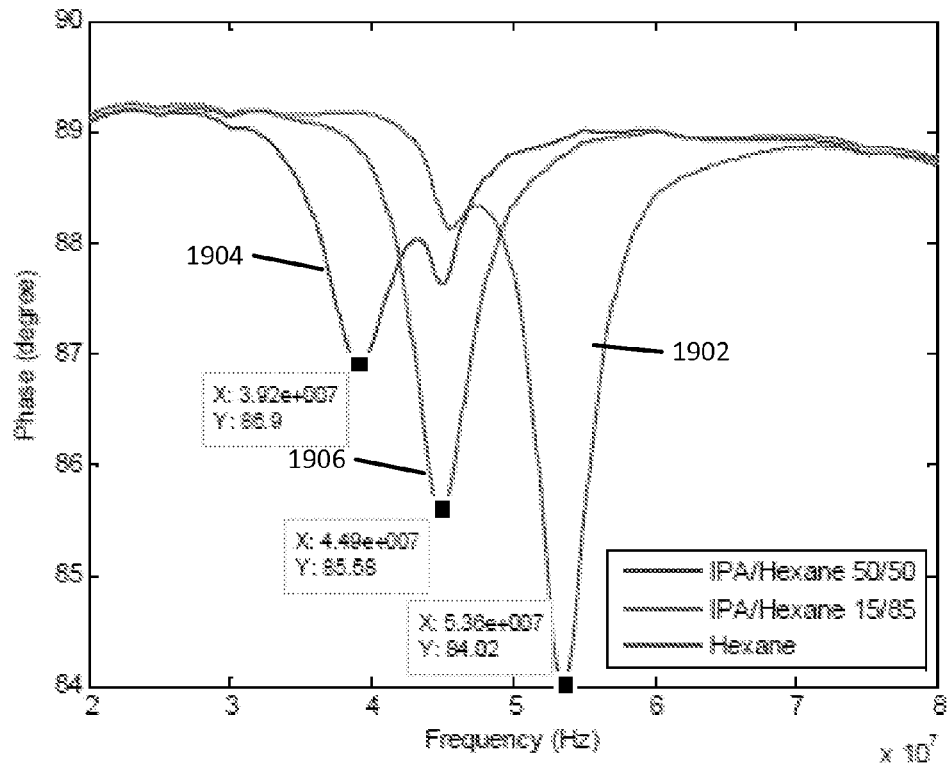
FIG. 20 is a graph showing the resonant frequency and phase angle dip of the uncoated nanowire fabric in the presence of various solvents.
Figure 21:
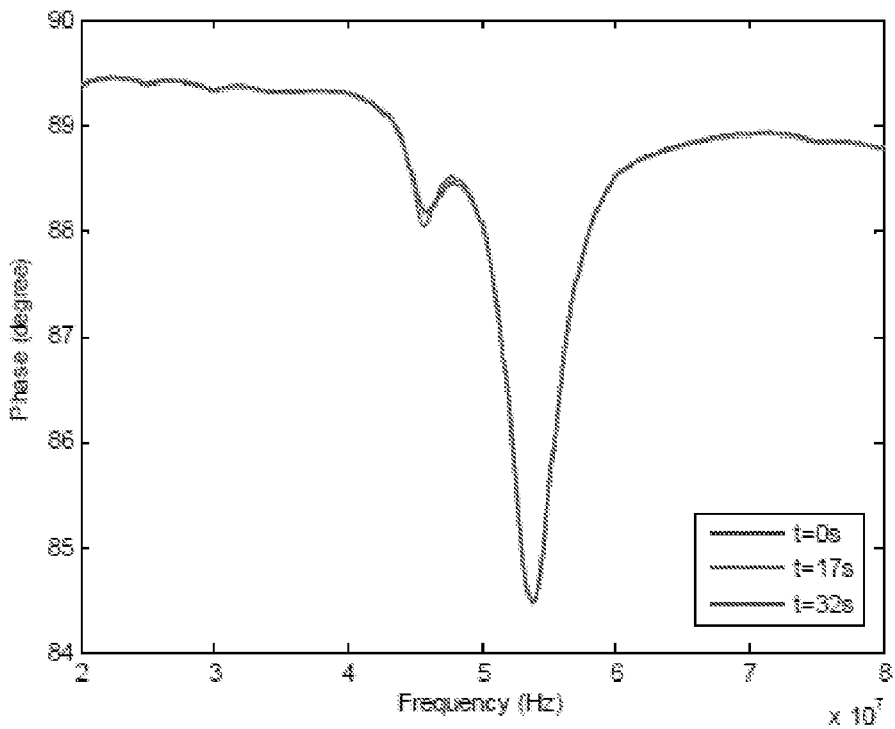
FIG. 21 is a graph showing the resonant frequency and phase angle dip of the sensor in accordance with one embodiment of the present invention with the coated nanowire fabric and the porous glass in the presence of hexane.
Figure 22:
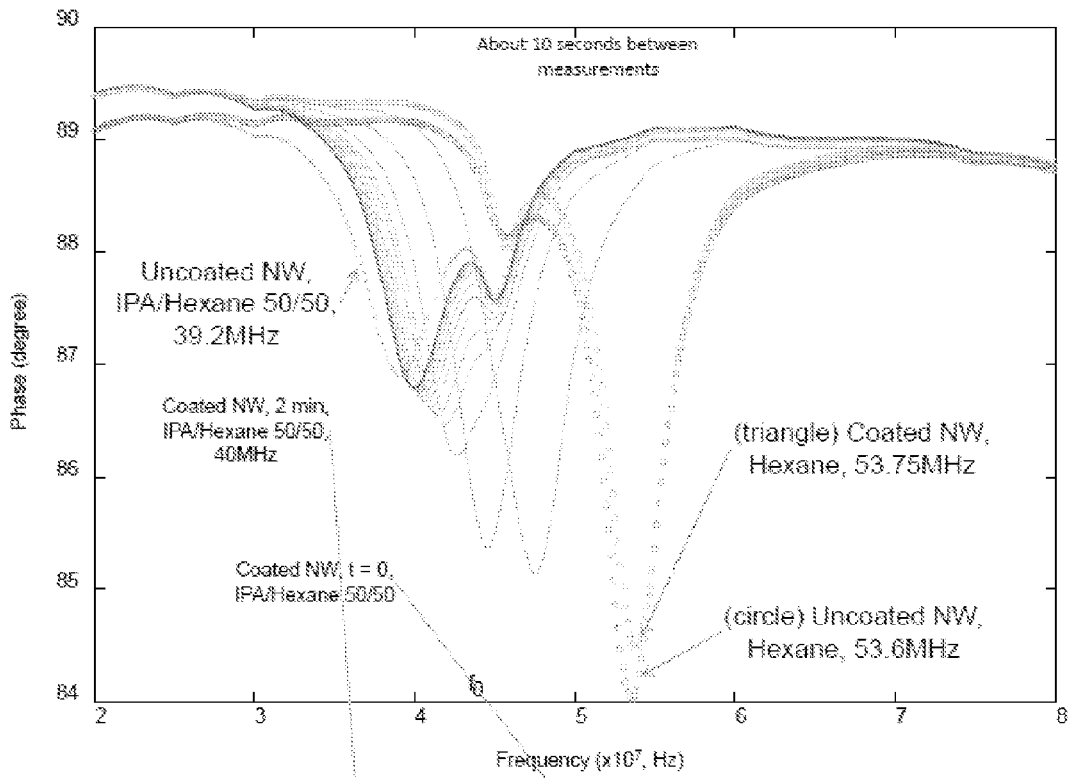
FIG. 22 is a graph showing the resonant frequency and phase angle dip of the sensor in accordance with one embodiment of the present invention with the coated nanowire fabric and the porous glass in the various solvents.

Now referring to FIG. 15, an exploded diagram showing a current setup 1500 used in testing a sensor 100 in accordance with the present invention is shown. The self-resonant sensor tag 106 is fabricated on a substrate 102 of quartz glass and coated with a passivation layer 104 of SU-8 insulation. FIGS. 16A-B are graphs showing measurements for the sensor 100 with and without the passivation layer 104 of SU-8 insulation for various materials under test (reader baseline 1600, DI water 1106, tap water 1308). The SU-8 insulation 104 prevents DC coupling to the material under test and allows the sensor 100 to sense materials under test with a higher conductivity. Experiments have shown no evidence of swelling or other changes in the SU-8 insulation 104 when immersed in solvents. The phase dip decreases in higher conductivity materials under test. Now referring back to FIG. 15, a high surface area material 108 (coated silicon nanoware fabric) is disposed on top of the passivation layer 104, and a porous glass filter disc 1502 is disposed over the high surface area material 108. The presence of the added layers (i.e., nanowires, glass frit cover and solvent) alters the capacitance of the sensor 100, which causes a change in the resonant frequency and phase angle dip as shown in FIG. 17 (isopropanol alcohol) and FIG. 18 (50% isopropanol alcohol and 50% hexane). Note that hexane does not dissolve the polymer coating on the silicon nanowire fabric 108, but isopropanol alcohol does dissolve the polymer coating. FIG. 19 is a graph showing the resonant frequency and phase angle dip of the sensor 100 in accordance with one embodiment of the present invention plus porous glass 1502 without the nanowire fabric 108 in the presence of various solvents (no solvent (reader baseline) 1900, hexane 1902, IPA/hexane 50/50 1904, IPA/hexane 15/85 1906). Note that the "secondary" peak is an artifact of the reader circuit. FIG. 20 is a graph showing the resonant frequency and phase angle dip of the uncoated nanowire fabric in the presence of various solvents (hexane 1902, IPA/hexane 50/50 1904, IPA/hexane 15/85 1906). The resonant frequencies are lower than those without the nanowire fabric. FIG. 21 is a graph showing the resonant frequency and phase angle dip of the sensor 100 in accordance with one embodiment of the present invention with the coated nanowire fabric 108 and the porous glass 1502 in the presence of hexane. There is no evidence of change over times 0 s, 17 s and 32 s, so the hexane does not dissolve the coating. FIG. 22 is a graph showing the resonant frequency and phase angle dip of the sensor 100 in accordance with one embodiment of the present invention with the coated nanowire fabric 108 and the porous glass 150 in the various solvents.

Figure 23:
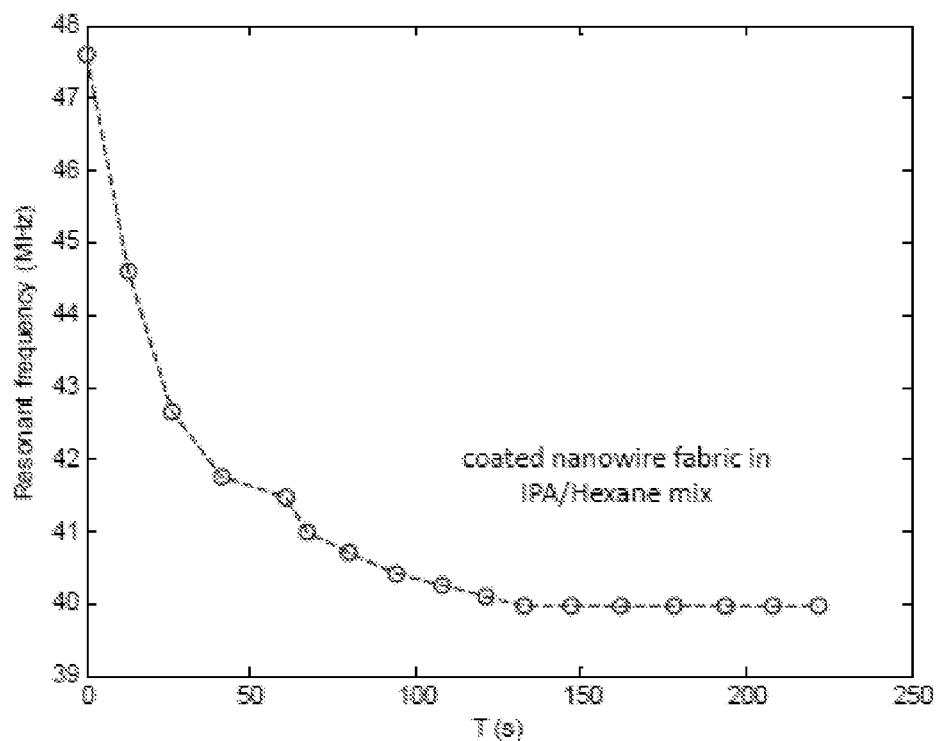
FIG. 23 is a graph showing the resonant frequency and time of the sensor in accordance with one embodiment of the present invention with the coated nanowire fabric in the 50% isopropanol alcohol and 50% hexane mix.
Figure 24A:
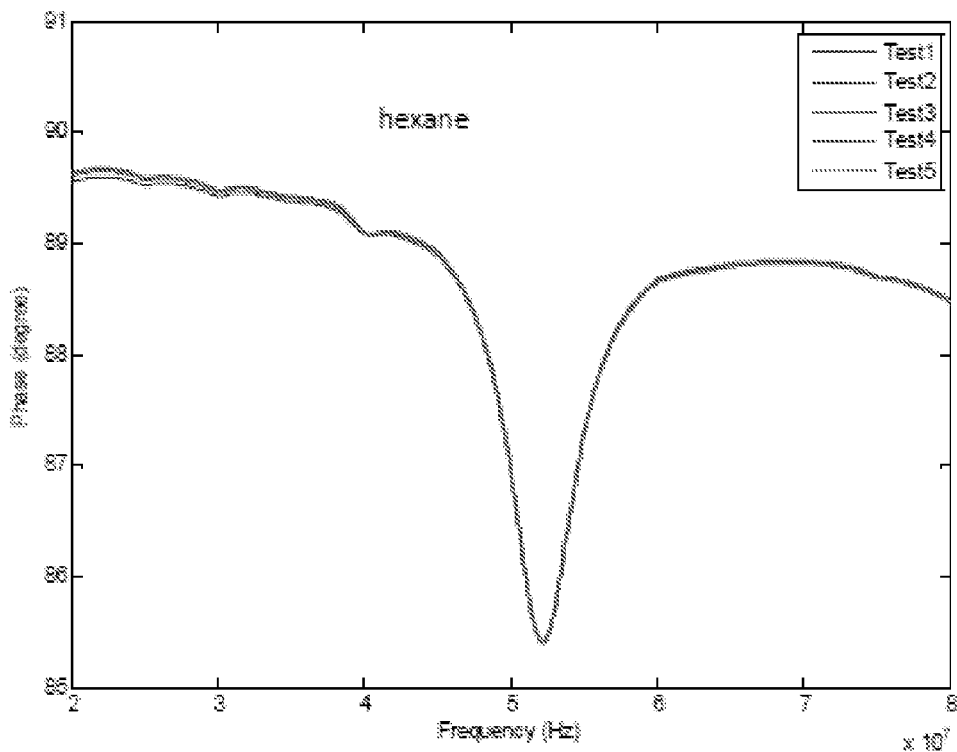
FIGS. 24A-B are graphs showing the resonant frequency and time of the sensor in accordance with one embodiment of the present invention with the coated nanowire fabric in hexane (FIG. 24A) and as isopropanol alcohol was added to achieve a 15% isopropanol alcohol and 85% hexane mix (FIG. 24B)
Figure 24B:
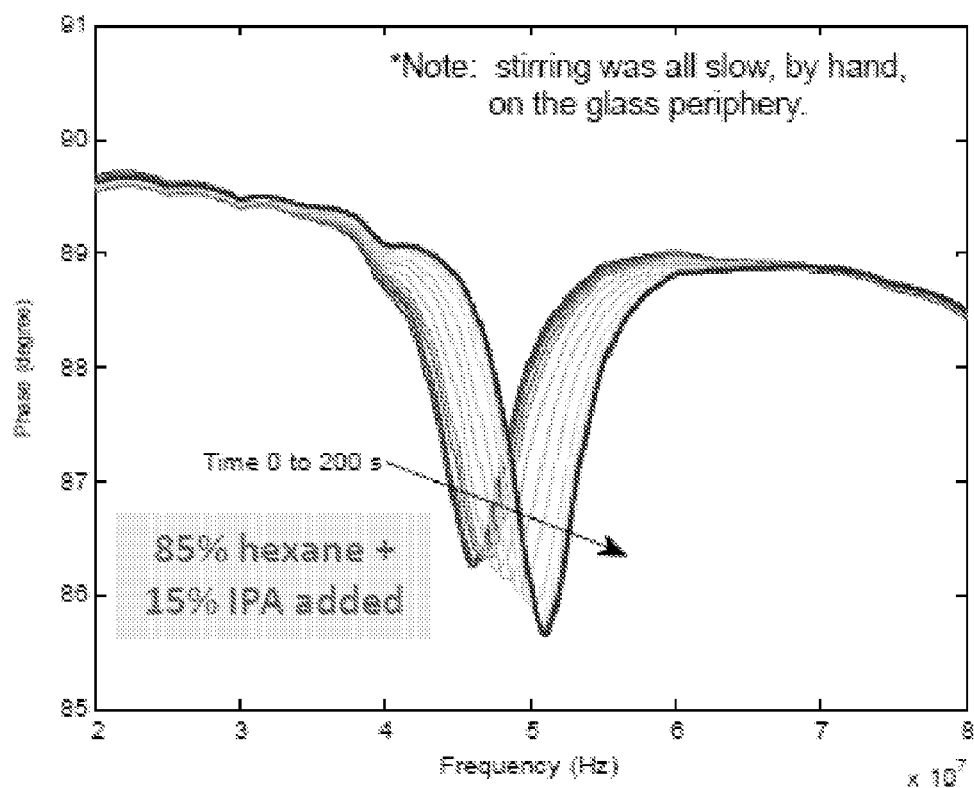
Figure 25:
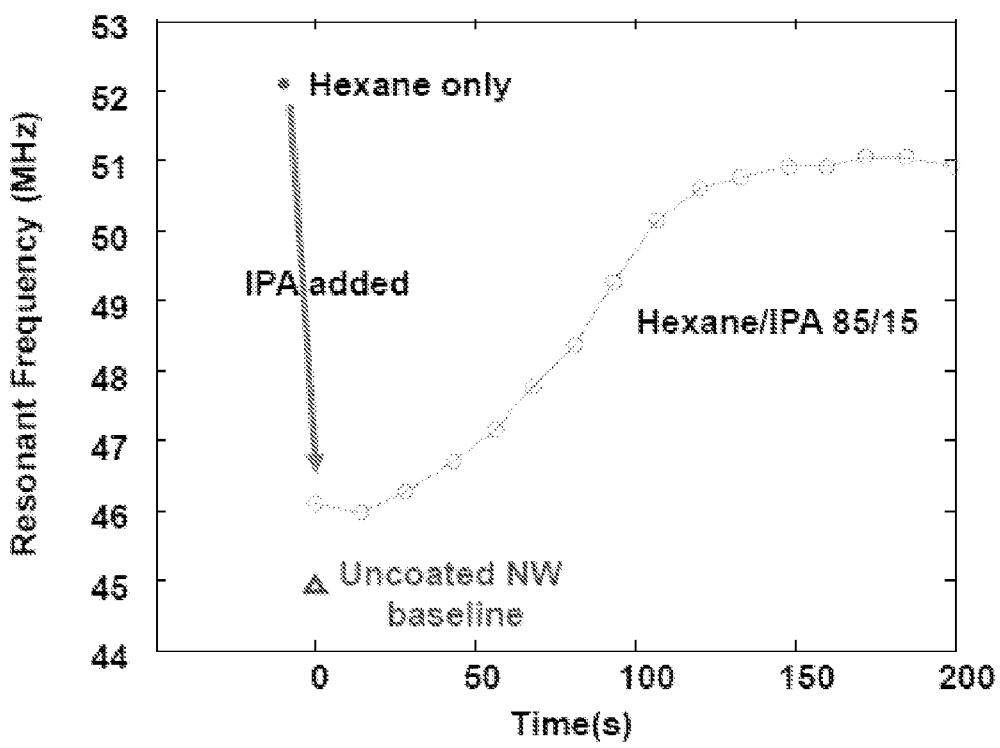
FIG. 25 is a graph shown the shift in resonant frequency over time in the test shown in FIG. 24B.
Figures 26, 27:
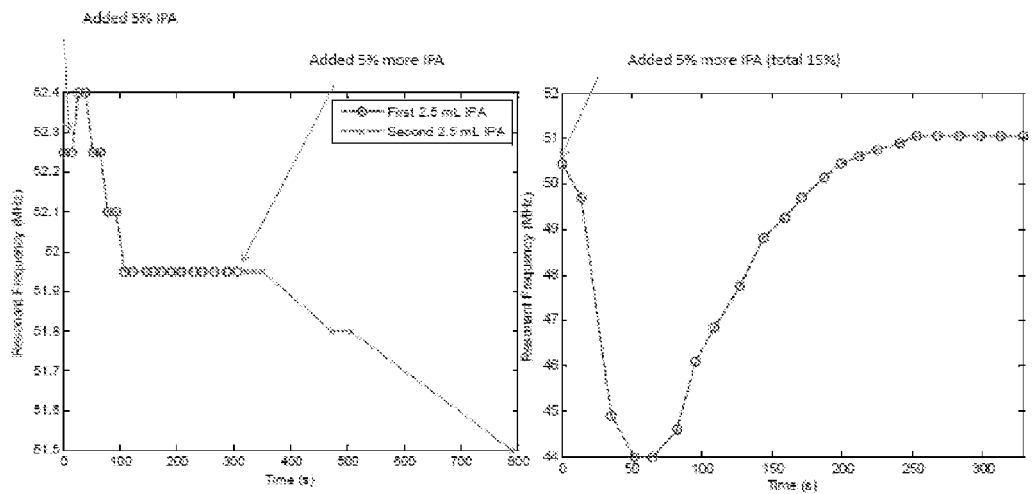
FIGS. 26 and 27 are graphs showing the resonant frequency and time of the sensor in accordance with one embodiment of the present invention with the coated nanowire fabric as more isopropanol alcohol is added to the hexane.

FIG. 23 is a graph showing the resonant frequency and time of the sensor in accordance with one embodiment of the present invention with the coated nanowire fabric in the 50% isopropanol alcohol and 50% hexane mix. This shows an approximate resonant frequency drop of about 16%. The relative dielectric constant of the 50% isopropanol alcohol (18) and 50% hexane (1.9) is approximately 9.9. FIGS. 24A and 24B are graphs showing the resonant frequency and time of the sensor in accordance with one embodiment of the present invention with the coated nanowire fabric in hexane (FIG. 24A) and as isopropanol alcohol was added to achieve a 15% isopropanol alcohol and 85% hexane mix (FIG. 24B). The peak was 52.1 MHz in hexane only. After the addition of the isopropanol alcohol, there was a fast shift to 46.1 MHz (approximately 15 seconds). Note that the baseline value is 44.9 MHz for uncoated nanowires in the 15% isopropanol alcohol and 85% hexane mix. There was a slower shift from 46.1 MHz to 50.9 MHz (200 seconds). FIG. 25 shows the shift in resonant frequency over time. The relative dielectric constant of the 15% isopropanol alcohol (18) and 85% hexane (1.9) is approximately 4.3. FIGS. 26 and 27 are graphs showing the resonant frequency and time of the sensor in accordance with one embodiment of the present invention with the coated nanowire fabric as more isopropanol alcohol is added to the hexane. The tests at 5% and 10% isopropanol alcohol showed only small shifts in frequency for the coated nanowires. At 15% isopropanol alcohol, there was a rapid decrease in frequency followed by a gradual increase.

Figures 28A, 28B:
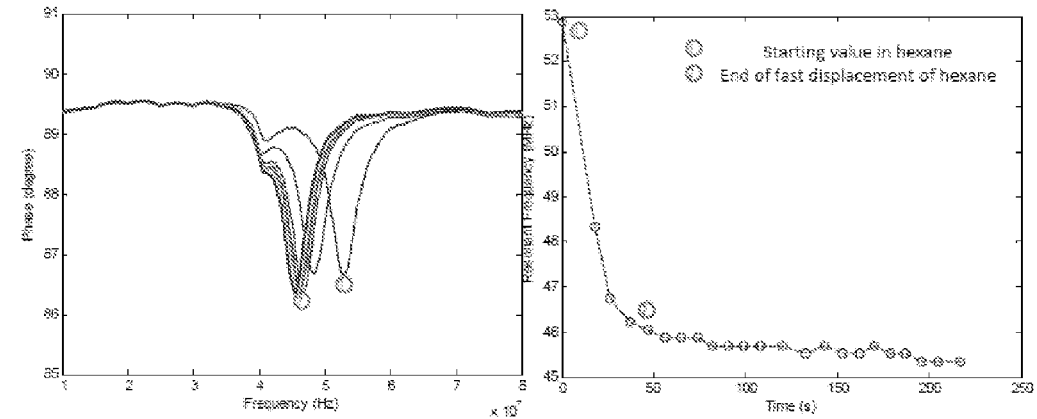
FIGS. 28A-B are graphs showing a bare nanowire baseline sensor test in accordance with one embodiment of the present invention.
Figures 29A, 29B:
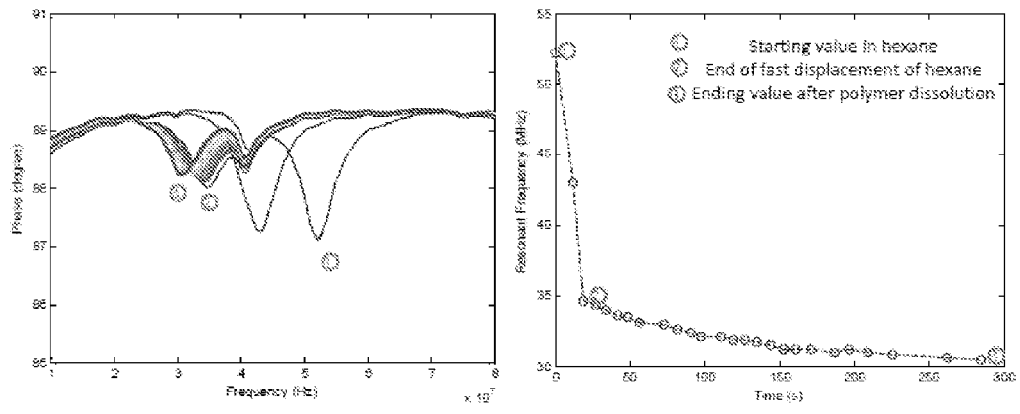
FIGS. 29A-B are graphs showing a sensor test with a nanowire mat having a 105 nm coating in accordance with one embodiment of the present invention.
Figure 30A:
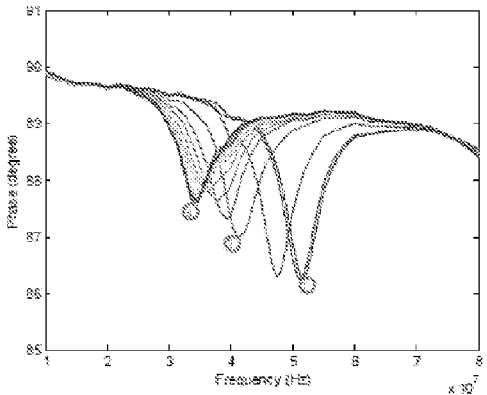
FIGS. 30A-B are graphs showing a sensor test with a nanowire mat having a 145 nm coating in accordance with one embodiment of the present invention.
Figure 30B:
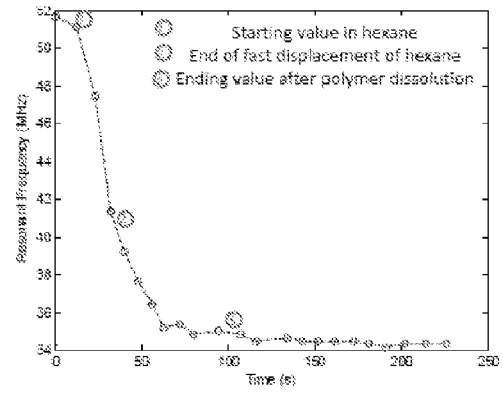
Figure 31A:
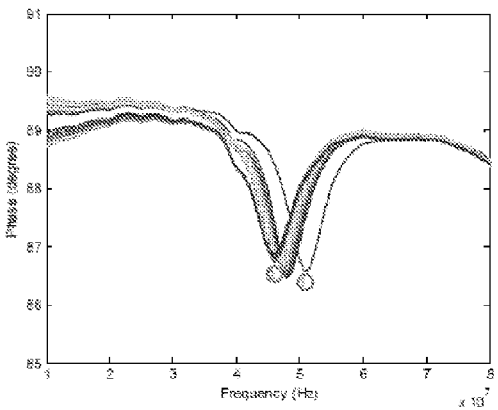
FIGS. 31A-B are graphs showing a sensor test with a nanowire mat having the 142 nm coating stripped off in accordance with one embodiment of the present invention.
Figure 31B:
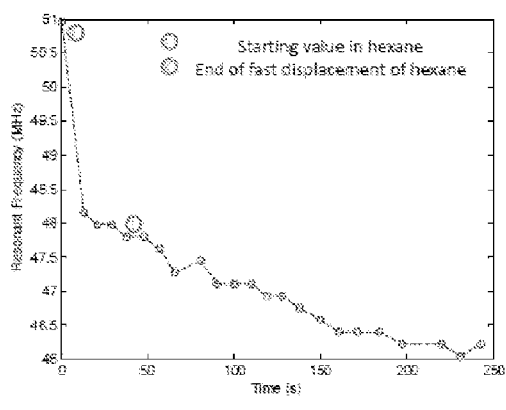

Additional tests were performed as follows. A clean nanowire mat was attached to the sensor via van der Waals adhesion (place on SRS tag, wet with toluene, allow to dry). The sensor and the nanowire mat were then coated in the iCVD reactor. The central square is shielded by Kapton tape, which is removed. A coarse glass frit was used to hold the device in place. The testing procedure involved: (1) immersion of the sensor in 55 mL hexane to establish a baseline; (2) 55 mL of water is added (gravity inverts the phases immediately); (3) data are collected as a function of time; and (4) timestamps from the file are used to plot data at approximately 10 seconds per reading. After one hexane-water cycle, the 'stripped' sensor was dried via nitrogen flow, and the cycle was repeated. The bare nanowire baseline sensor test is shown in FIGS. 28A and 28B. There was a quick shift in the first 20-30 seconds as the bulk hexane is displaced by the water and little or no drift after 30 seconds. The endpoint frequency was much nearer the hexane value than water, which is indicative of capillary forces retaining hexane within the sensor. There was no driving force to push the hexane out or the water in within the sensing region. The sensor test with a nanowire mat having a 105 nm coating is shown in FIGS. 29A and 29B. There was a quick shift in the first 20 seconds as the bulk hexane is displaced by the water. The frequency shift is much greater as the hydrophilic polymer pulls in water and displaces the hexane. A slower drift of 4 MHz occurred over the next five minutes as the polymer dissolves and is replaced by the bulk liquid surrounding it (water). The lower endpoint frequency versus the bare nanowire shows the hydrophilic coating is very important for drawing water into the sensing region. The sensor test with a nanowire mat having a 145 nm coating is shown in FIGS. 30A and 30B. There was a quick shift in the first 20 seconds as the bulk hexane is displaced by water. The thicker coating means less hexane is displaced as compared to a thinner coating. A more significant polymer dissolution occurred between 20 and 100 seconds as compared to a thinner coating due to water dissolving and replacing the polymer. The endpoint frequencies of both tests were consistent. The dynamics are different for different polymer thicknesses. As a result, the sensor can be tuned by varying the polymer thickness. The sensor test with a nanowire mat having the 142 nm coating stripped off is shown in FIGS. 31A and 31B. This test had virtually identical results as the bare nanowire test. There was only a small, quick change due to water replacing the hexane. The frequency endpoints and dynamics are consistent with the bare nanowire test showing that the coating has in fact been removed.

Figure 32A:
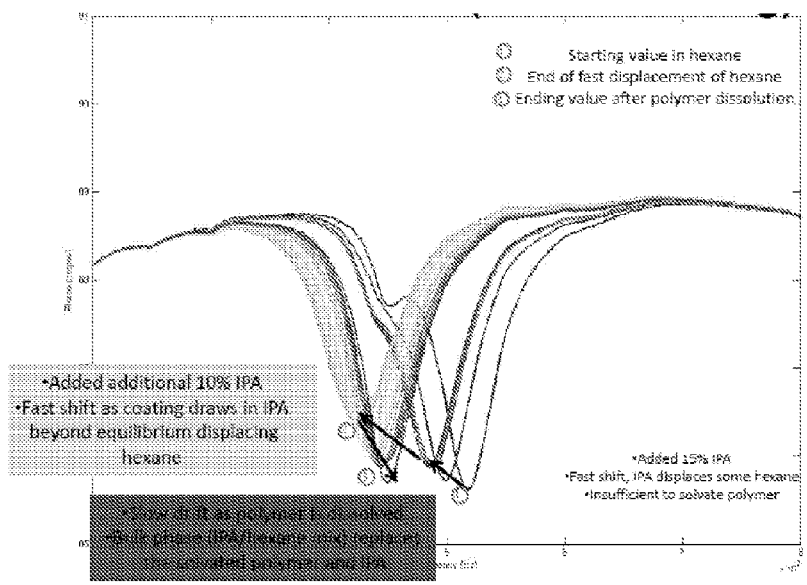
FIGS. 32A-B are graphs showing tests of the sensor with a 25 nm coating of poly-4-vinylpyridine starting with 100% hexane and adding isopropanol alcohol in accordance with one embodiment of the present invention.
Figure 32B:
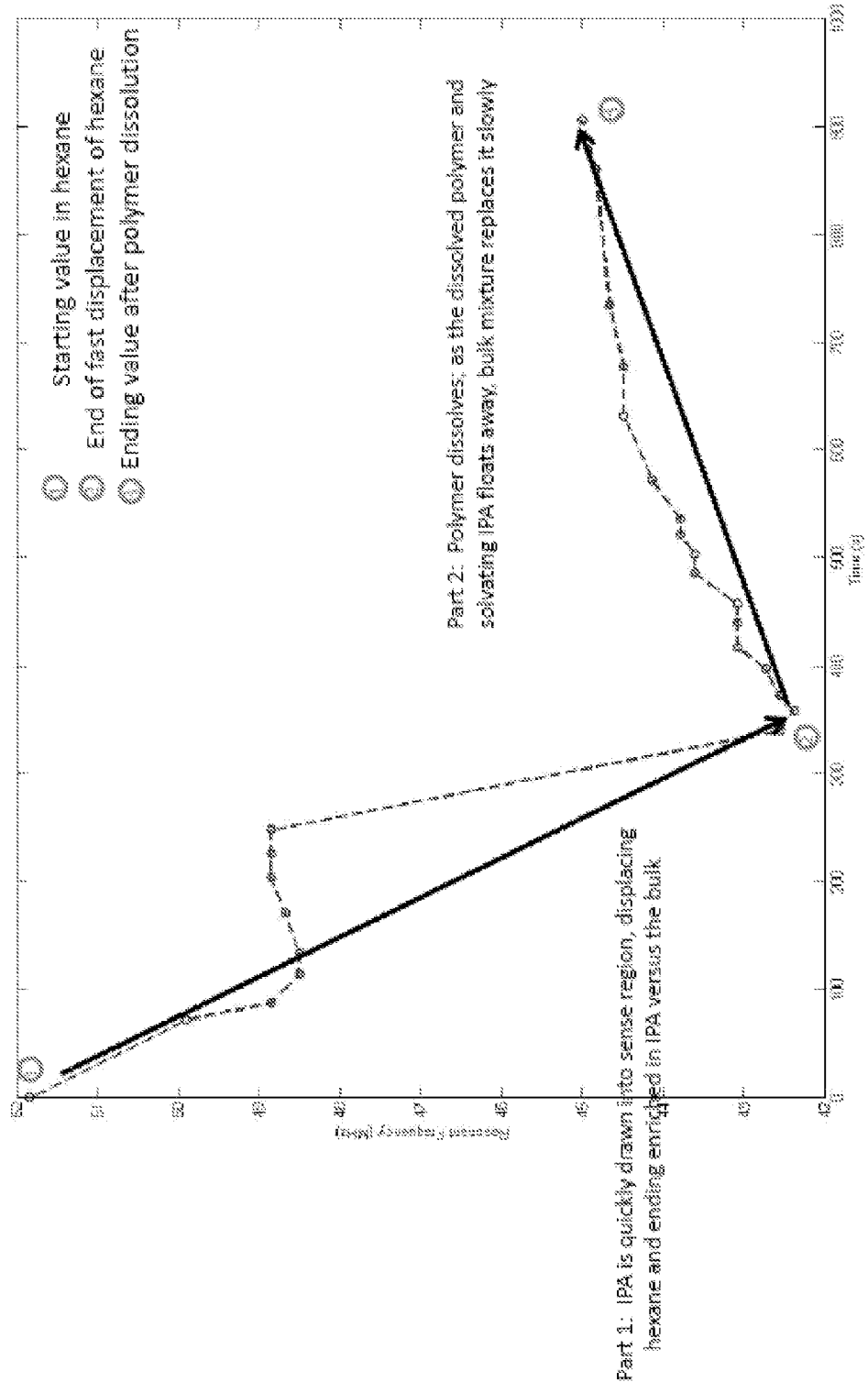

FIGS. 32A and 32B shows tests of the sensor with a 25 nm coating of poly-4-vinylpyridine starting with 100% hexane and adding isopropanol alcohol. The foregoing tests show that the sensor device can detect the difference between water and hydrocarbon using polyacrylic acid. The exposure to water resulted in a rapid displacement of bulk hexane by water, followed by a slower dissolution period. The polymer coating of the sensor increases the magnitude of response to water. A variation of polymer thickness significantly changes the dynamic response of the sensor.

Capillary forces and polymer dissolution are two different physical effects due to the coating. The large, tortuous channels between wires act like narrow capillaries. If surfaces of nanowires are relatively hydrophobic as a consequence of synthesis, and no external pressure is applied, hexane in the interior is not removed when water is introduced. This leads to the much higher endpoint frequency. In contrast, the interior of a polyacrylic acid-coated silicon nanowire mat is very hydrophilic. This chemical affinity serves to pull in water and displace hexane. As a result, the frequency at end is much lower and more consistent with the value expected from water. These bulk solvent replacements are very rapid. The polymer dissolution effect is evident by slower changes occurring after 30 seconds. Water is slowly dissolving polymer. As a result, the volume occupied by lower-dielectric polymer is replaced by higher-dielectric water. This produces a slow shift downward in the thinner-coated mats.

Figure 33A:
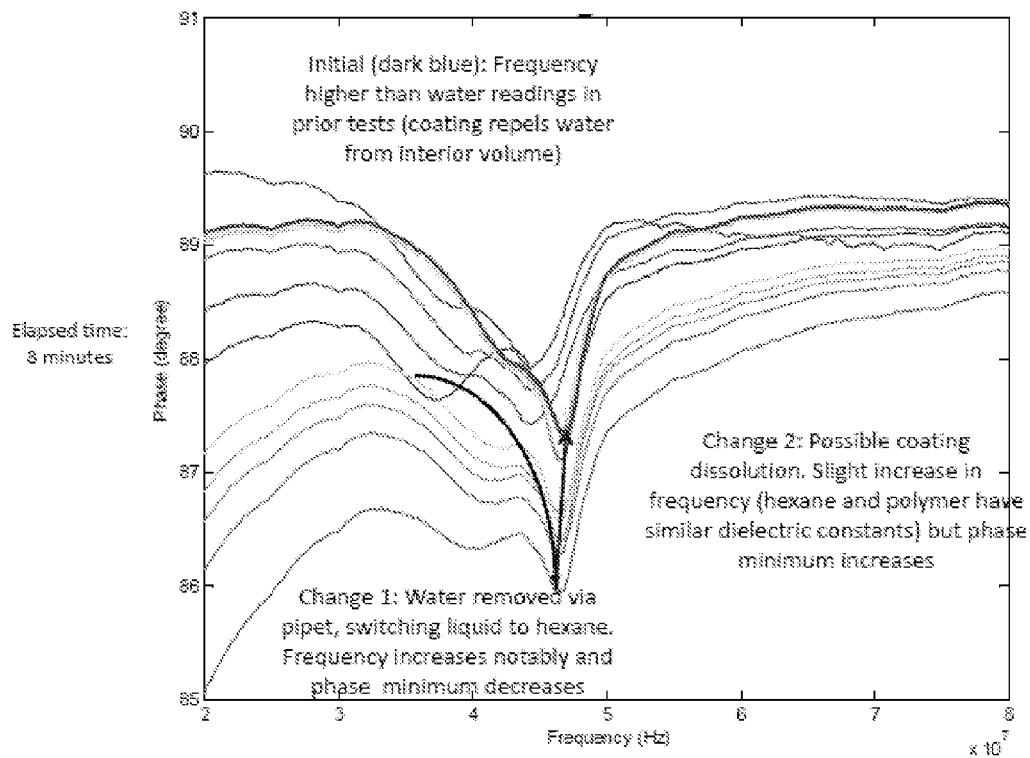
FIGS. 33A-B are graphs showing tests of the sensor with a hexyl acrylate coating and after the coating is stripped off in accordance with one embodiment of the present invention.
Figure 33B:
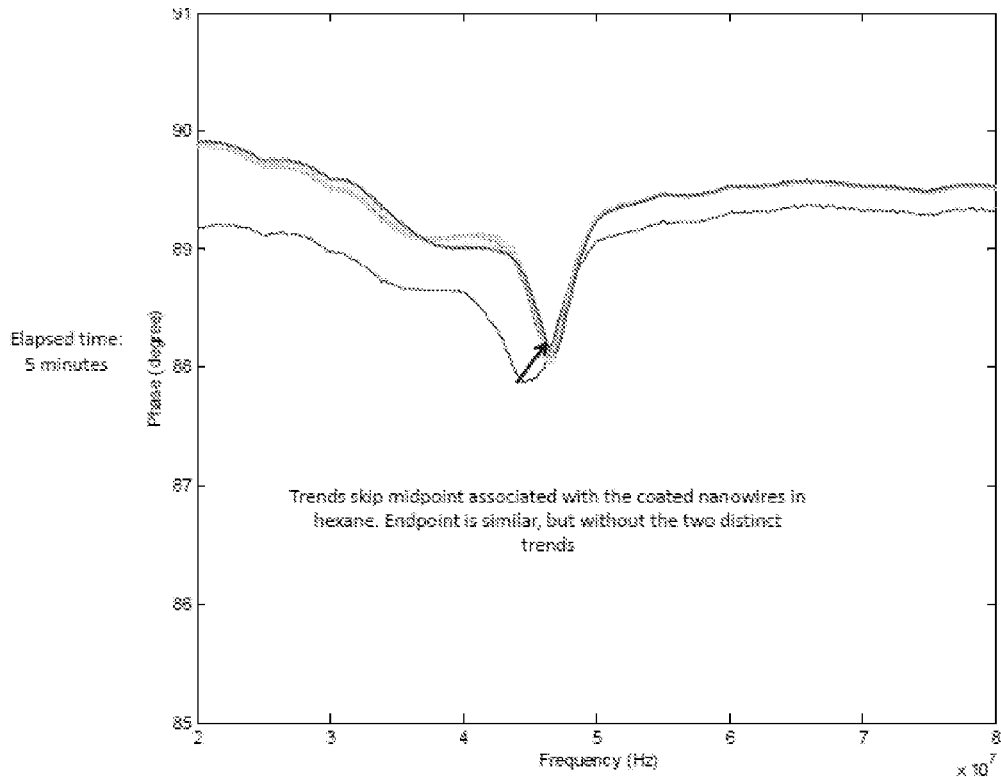

A new test was developed in which the sensor is covered with water. Hexane is added on top of the water and the water is removed so that the hexane replaces the water as the sensing liquid. This platform allows real time dynamic observations that are virtually impossible to observe with any other technique together, these results show a powerful potential for building a scalable platform for sensing. The capillary concept shows that the sensor shows not only a large change in resonant frequency (in comparison to uncoated wires) but retains a memory of this even after the condition is removed. This is a capability that allows substantially more tuning than could be hoped for with a soluble layer without the capillary structure. In addition, it would allow the use of the sensor in constrained geometries since a limited contact area would only amplify these capillary-like effects. A hexyl acrylate monomer coating can be used for a water to aliphatic hydrocarbon sensor. A benzyl methacrylate monomer coating can be used for a water to aromatic hydrocarbon sensor. A crosslinked or reversible sensor can be made by adding ethylene glycol diacrylate monomer at low vapor pressure. FIGS. 33A and 33B shows tests of the sensor with a hexyl acrylate coating and after the coating is stripped off. The coated sensor changes dynamics and introduces a midpoint value prior to coating dissolution. The endpoint value is fairly similar for both.

Figure 34:
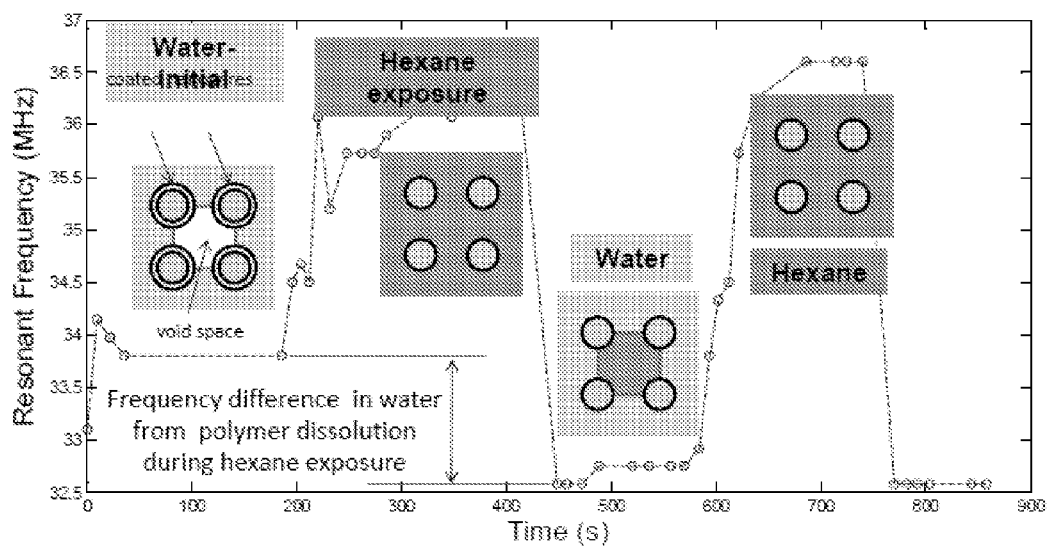
FIG. 34 is a graph showing a test of a hydrocarbon sensor with hydrophobic pHA coating in accordance with one embodiment of the present invention.

FIG. 34 shows a test of a hydrocarbon sensor with hydrophobic poly hexyl acrylate ("pHA") coating. The sensor was cycled between water and hexane while making in situ measurements. The hexane dissolves the coating and the mesh void space is filled by the hexane. The resonance is ~36.5

MHz regardless of prior exposure history. The value in water depends on prior exposure to hexane. If the coating is never exposed to hexane, the polymer excludes volume, and water only partially fills the hydrophobic interior of nanowire mesh. The resonance is ~33.7 MHz. Exposure to hexane dissolves the coating and more water incorporated in mesh causing a shift to ~32.5 MHz. The sensor retains a memory of chemical history: "start" state @ 33.7 MHz and "triggered" state @ 32.5 MHz.

As shown in FIG. 35, the sensor 3500 may also include a cavity 3502 disposed within the substrate 102 proximate to a center of the planar spiral inductor 110, and a ferrite core 3504 disposed in the cavity 3502. Alternatively, the substrate 102 can be a flexible substrate such that the flexible substrate is rolled to form a coil having a central void. A ferrite core can be disposed within or through the central void of the coil.

Figure 36C:
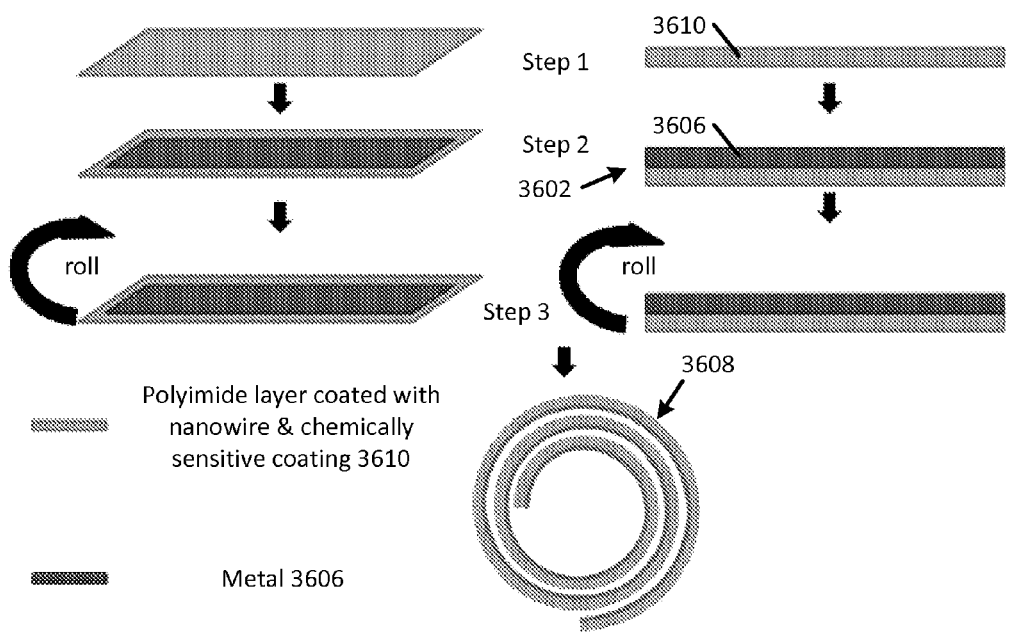
Figure 36D:
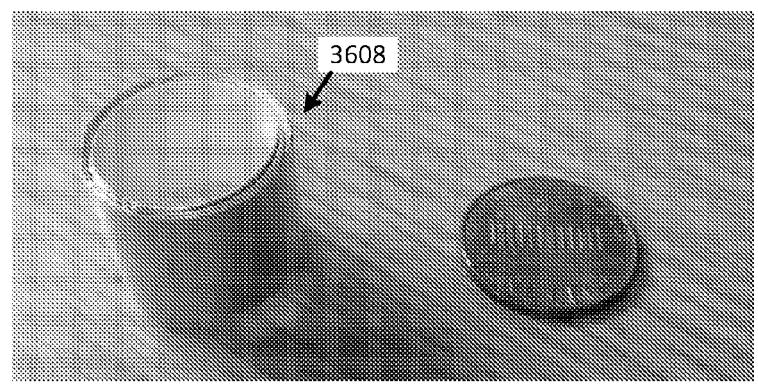
Figure 37:
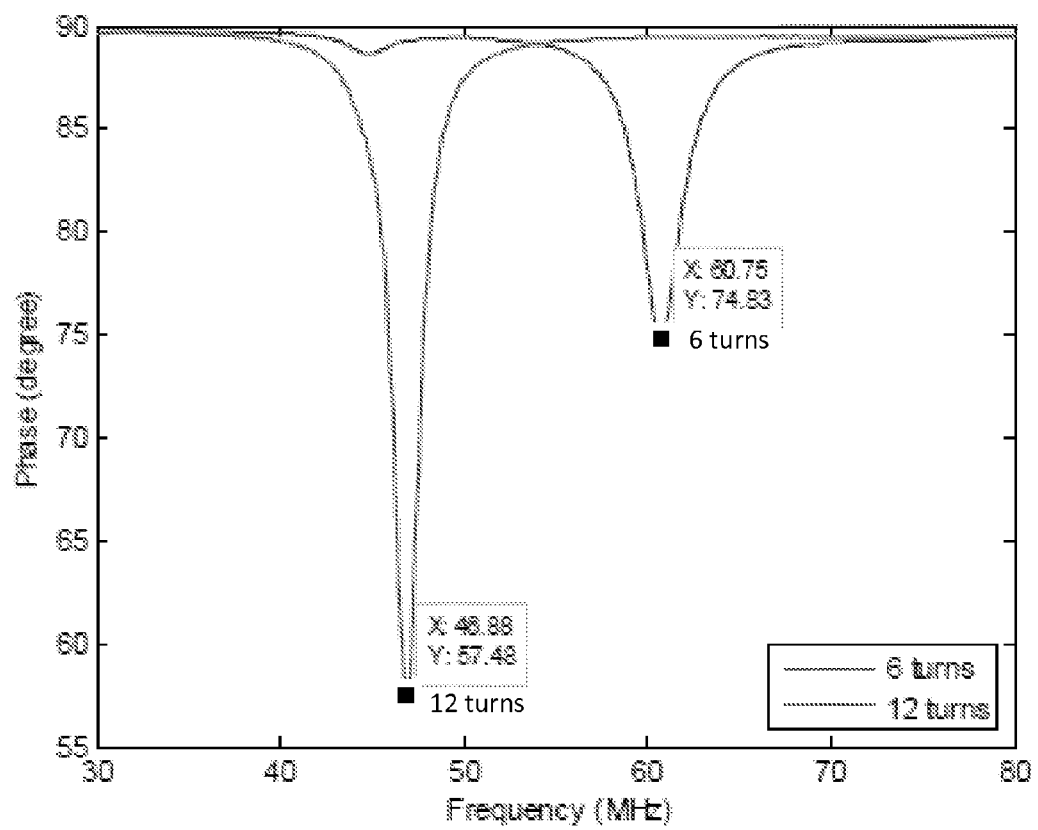
FIG. 37 shows the resonant frequency and phase dip of the "jelly roll" coil having 6 and 12 turns in accordance with one embodiment of the present invention.

Another self-resonant sensor 3600 will now be described. As shown in FIGS. 36A-D, a "jelly roll" sensor 3600 for detecting one or more materials is shown. FIG. 36A shows a cross section of an unrolled "jelly roll" sensor wherein the self-resonant structure 3602 includes an elongated flexible substrate strip 3604, an electrically conductive trace 3606 disposed on the elongated flexible substrate strip 3604, and a high surface area material 108 (e.g., nanowire fabric) disposed on the elongated flexible substrate strip 3602 and electrically conductive trace 3606. The electrically conductive trace 3604 is formed on the elongated flexible substrate 3602 proximate to a centerline of the elongated flexible substrate strip 3602. The sensor 3600 is then formed by rolling the self-resonant structure 3602 into a coil 3608 having a central void with a ferrite core 3504 disposed within or through a central void of the coil 3608 (FIG. 36B). The high surface area material 108 includes a conformal polymer coating to increase a sensitivity to the one or more materials. As shown in FIG. 36C, the self-resonant structure 3602 may include a flexible substrate 3604 made of polymide coated with a high surface area material 108 made of nanowire and a chemically sensitive coating (collectively referred to as "coated nanowire 3610"), and a metallic layer 3606 (electrically conductive trace). The self-resonant structure sensor 3600 is fabricated by: (Step 1) providing the coated nanowire 3610; (Step 2) depositing the metallic layer 3606 on the coated nanowire 3610; and (Step 3) rolling the self-resonant structure 3602 (3610 and 3606) into a coil 3608. The self-resonant structure 3602 (3610 and 3606) can also be rolled around a ferrite core 3504 (see FIG. 36B). FIG. 37 shows the resonant frequency and phase dip of the "jelly roll" coil 3608 having 6 and 12 turns. The 6 turn "jelly roll" coil 3608 has a resonant frequency of 60.75 MHz and a pseudo Q of 21.401 degrees. The 12 turn "jelly roll" coil 3608 has a resonant frequency of 46.88 MHz and a pseudo Q of 31.907 degrees.

The self-capacitance and inductance of the "jelly roll" sensor are distributed in a complex way. For example, measurements of the 12 turn "jelly roll" sensor showed a self-resonant frequency of 37 MHz. When a 330 pF capacitor (>>self capacitor) was connected between the ends of the roll, the resonance frequency dropped. This configuration forced current to flow through ALL turns of the rolled coil. The inductance calculated from the new resonant frequency was 1.26 µH. From (37 MHz, 1.26 µH), the calculated 'effective' self-capacitance was 21.9 pF. This is much less than expected since the separation between windings was only 37.5 µm. The total parallel plate capacitance should be in the nF range. This is due to the distributed nature of the whole coil, leading to "non-uniform" current distribution from one turn to the next. Both the effective inductance and effective capacitance are reduced. As shown below, the inductance increased when the width of the strip was decreased even though intuitively the inductance should have remained about the same. The effective capacitance deceased by 4× and the resonance frequency increased, but not by 4×. For reference, the inductance of a 12 turn and 6 turn solenoid if 2.2 µH and 0.80 µH, respectively.

| | Resonance frequency | "Measured" inductance | "Measured" self capacitance |
|---|---|---|---|
| 1× width (12 turns) | 30.319 MHz | 1.2578 µH | 21.9 pF |
| 1× width (6 turns) | 43 MHz | 0.34878 µH | 37.857 pF |
| ¼× width (12 turns) | 37 MHz | 3.1433 µH | 5.861 pF |
| ¼× width (6 turns) | 57.7 MHz | 0.74404 µH | 10.226 pF |

Figure 38:
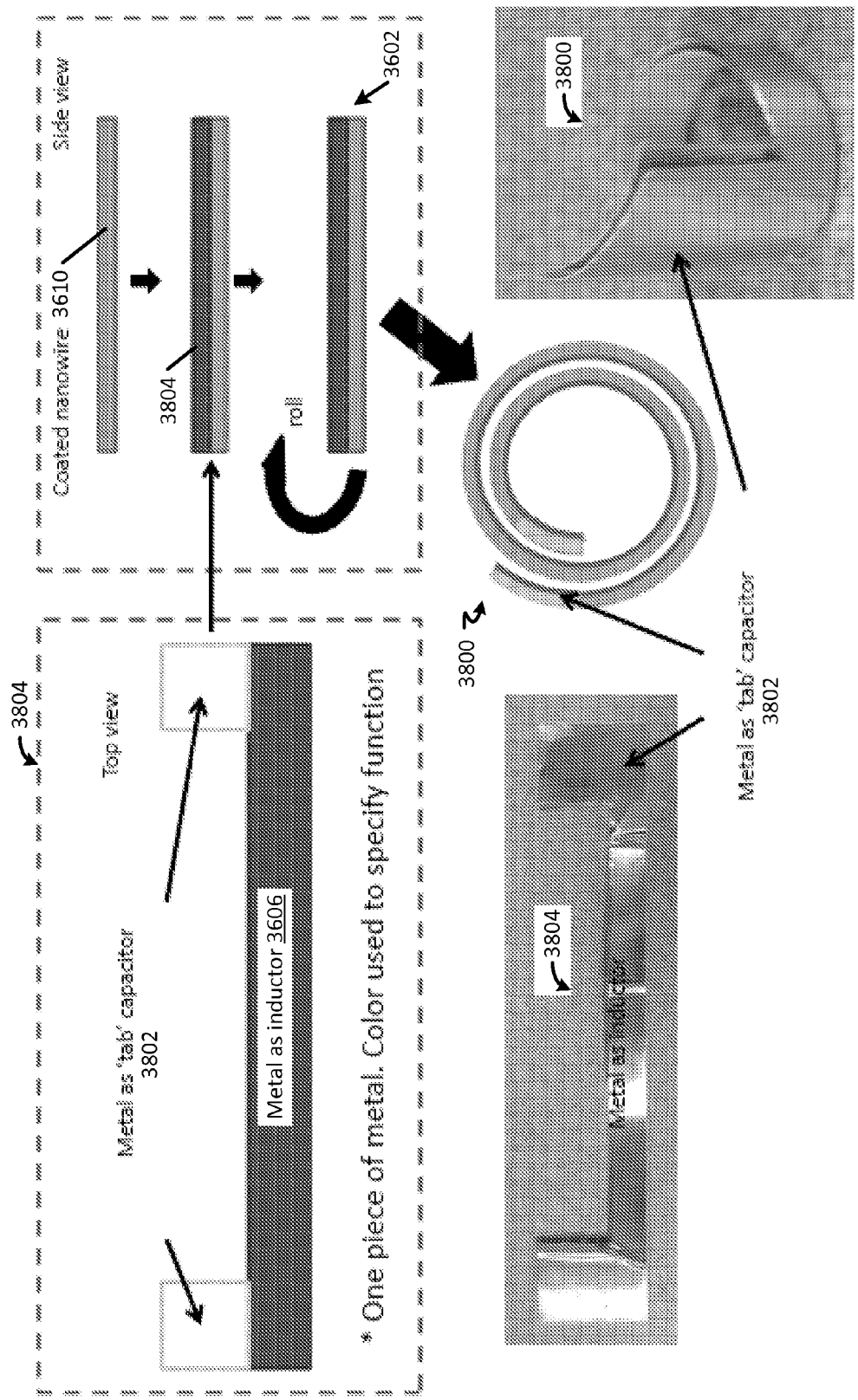
FIG. 38 shows the "jelly roll" coil with the tab capacitor in accordance with another embodiment of the present invention.

Since the inductance increases with decreasing width of the strip, this is good news for miniaturization. The distributed nature still makes capacitance smaller than its simple geometry would suggest (not 'efficient'). As a result and as shown in FIG. 38, a metal tab 3802 can be attached to each end of the electrically conductive trace 3606 such that the capacitance is well controlled and simplified manufacturing is still allowed. In other words, "jelly roll" coil 3800 is the "jelly roll" coil 3608 with tab capacitors 3802. Fabrication of the "jelly roll" coil 3800 is the same as the "jelly roll" coil 3608 except that the electrically conductive trace 3606 includes tabs 3802 (collectively 3804). The tabs 3802 increase the effective capacitance of the sensor by the amount of the parallel capacitance of the tab 3802 and the resonance frequency is decreased.

| | Resonance frequency | "Measured" inductance | "Measured" self capacitance |
|---|---|---|---|
| Without tab | 57.7 MHz | 0.74 µH | 10.23 pF |
| With tab | 31.3 MHz | 0.74 µH | 34.75 pF |

Figure 39:
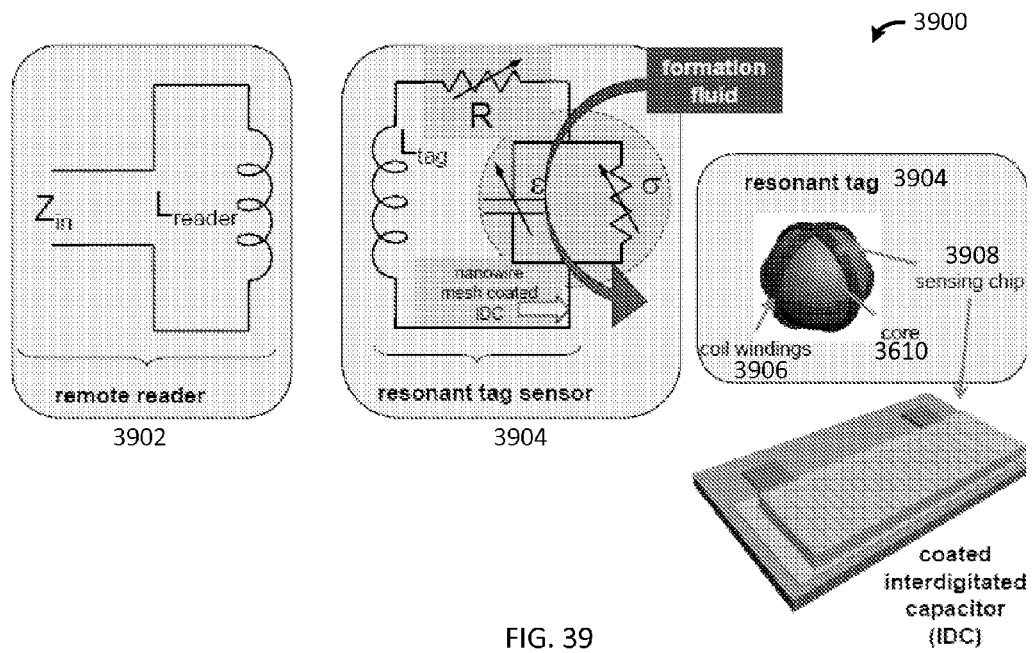
FIG. 39 shows a passive chemically sensitive resonant tag system in accordance with yet another embodiment of the present invention.

For a fixed volume, the design considerations are (1) increase the number of turns as much as possible (inductance is proportional to $N^2$), (2) decreasing height increases inductance, but sacrifices self-capacitance, and (3) using the space freed by reducing height (width of the strips), the 'tabs' can act as the main transducer. The tabs 3802 provide more control and it is easier to interpret the capacitance value. The tab capacitance needs to be much greater than the self-capacitance by designing dielectric thickness. The coupling factor also needs to be considered although initial measurements suggest this was not a big problem. A 1 mm "jelly roll" coil 3800 can be scaled down using these criteria:

10 turn, 25 µm thick metal, 25 µm thick insulator
Internal diameter=0.1 mm, outside diameter=1.1 mm
Trace width=0.5 mm
Tab size=0.5 mm×0.5 mm, capacitance=0.88 pF (∈=10)
Self-cap=0.16 pF (∈=10)
L=0.44 µH (actual L may be smaller based on macro jelly roll observation)
Resonance frequency=755 MHz Now referring to FIG. 39, a passive chemically sensitive resonant tag system 3900 is shown in accordance with yet another embodiment of the present invention. The models for the remote reader 3902 and the resonant tag sensor 3904 are shown. The resonant sensor tag 3904 can be any of the embodiments previously described or coil windings 3906 wrapped around a core 3610 and a sensing chip 3908 electrically connected to the coil windings 3906. The sensing chip can be an IDC sensor 3906 with a high surface area material having a conformal polymer coating attached thereto. The model of the resonant tag sensor 3904 is a simple RLC resonant circuit (similar to EAS tags) that is inductively coupled to remote reader 3902 and is suitable for use in harsh environments. Transduction causes change in resonance frequency shifts and Q changes. Nano-wire based devices for chemical sensing use coated nano-wires incorporated into ESS tag platform to allow remote-read.

Figure 40:
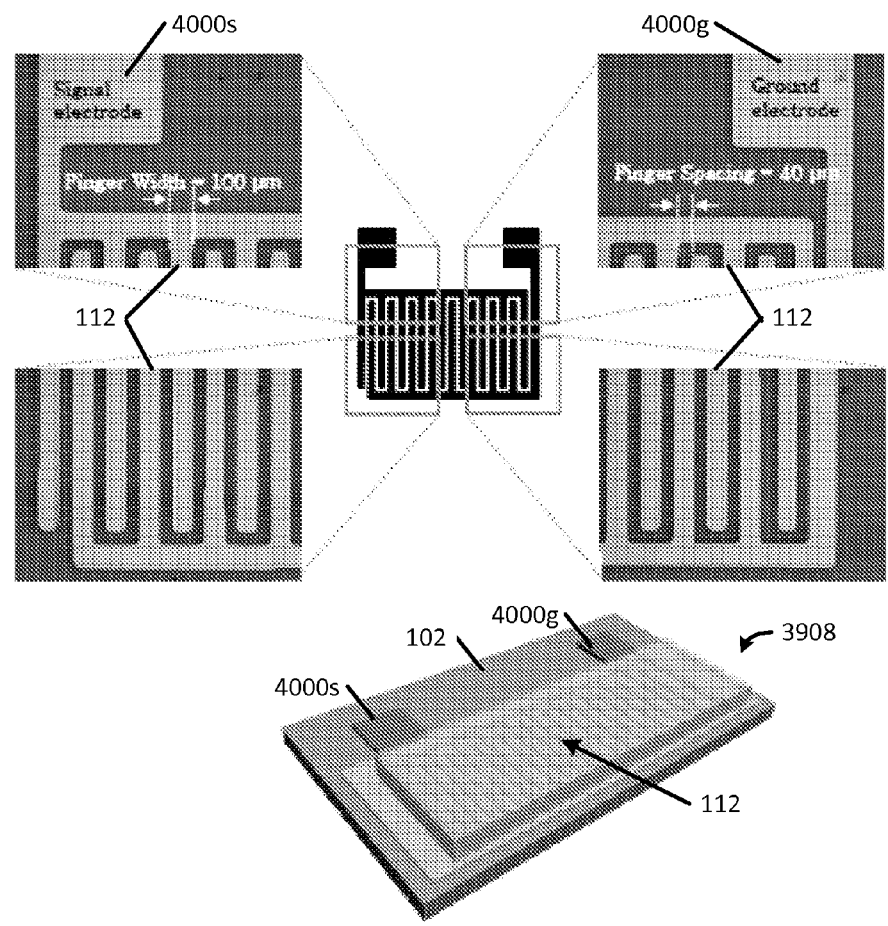
FIG. 40 shows a passive chemically sensitive resonant IDC sensor in accordance with yet another embodiment of the present invention.
Figure 41:
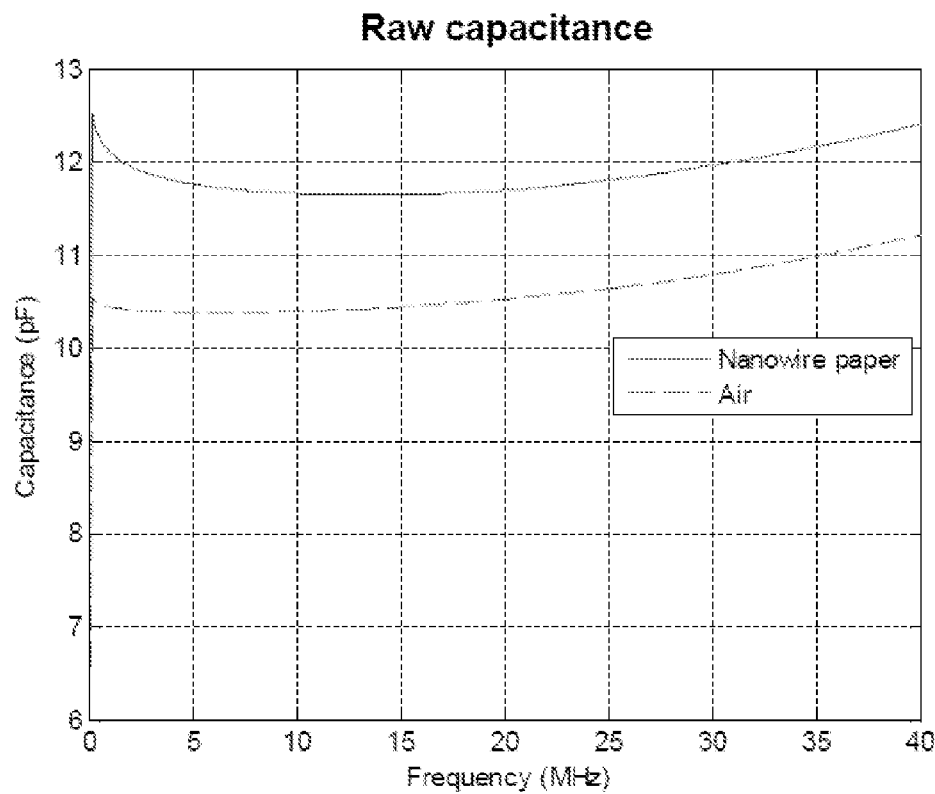
FIGS. 41-43 are graphs showing the raw capacitance (FIG. 41), shunt conductance (raw) (FIG. 42), and loss tangent (ration of conduction current to displacement current) (FIG. 43) of the nanowire paper and air in accordance with one embodiment of the present invention.
Figure 42:
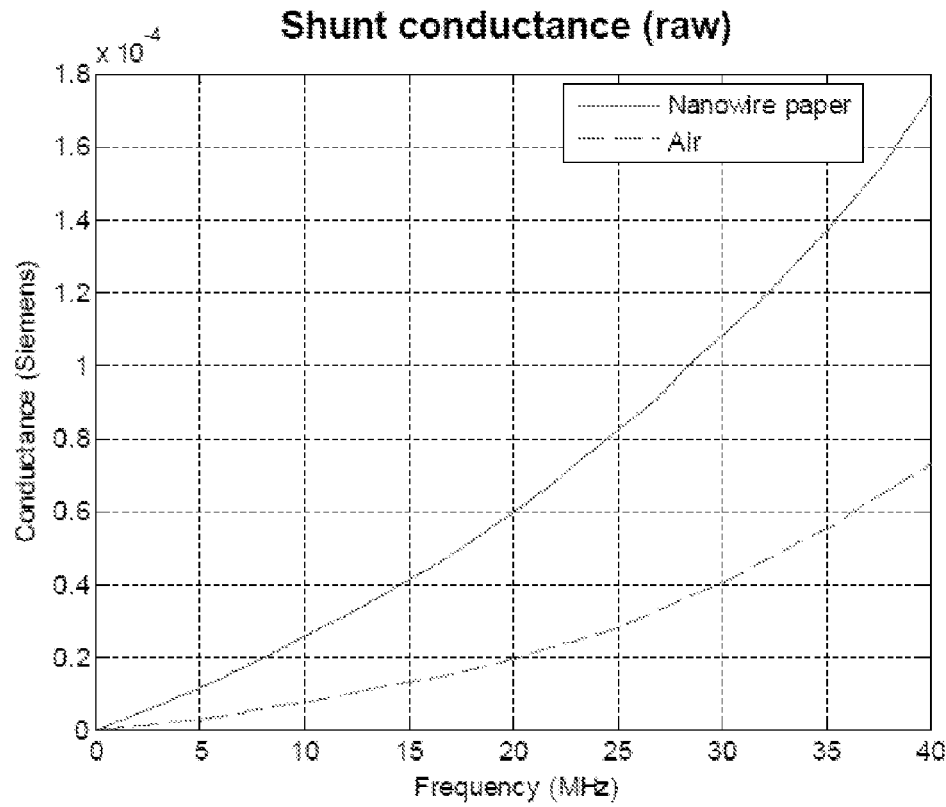
Figure 43:
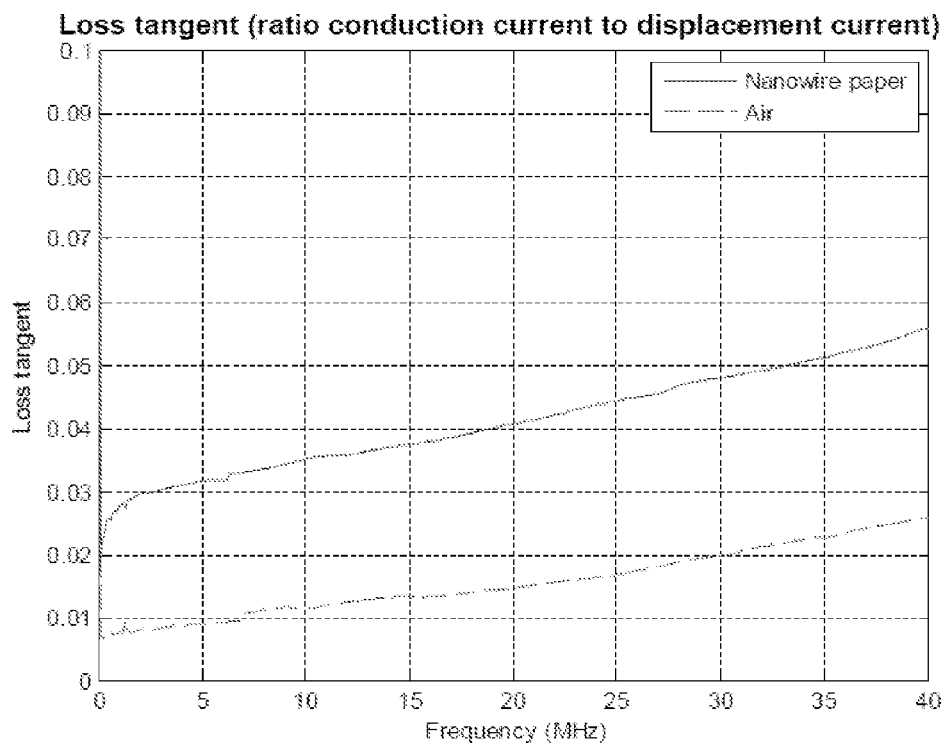
Figure 44:
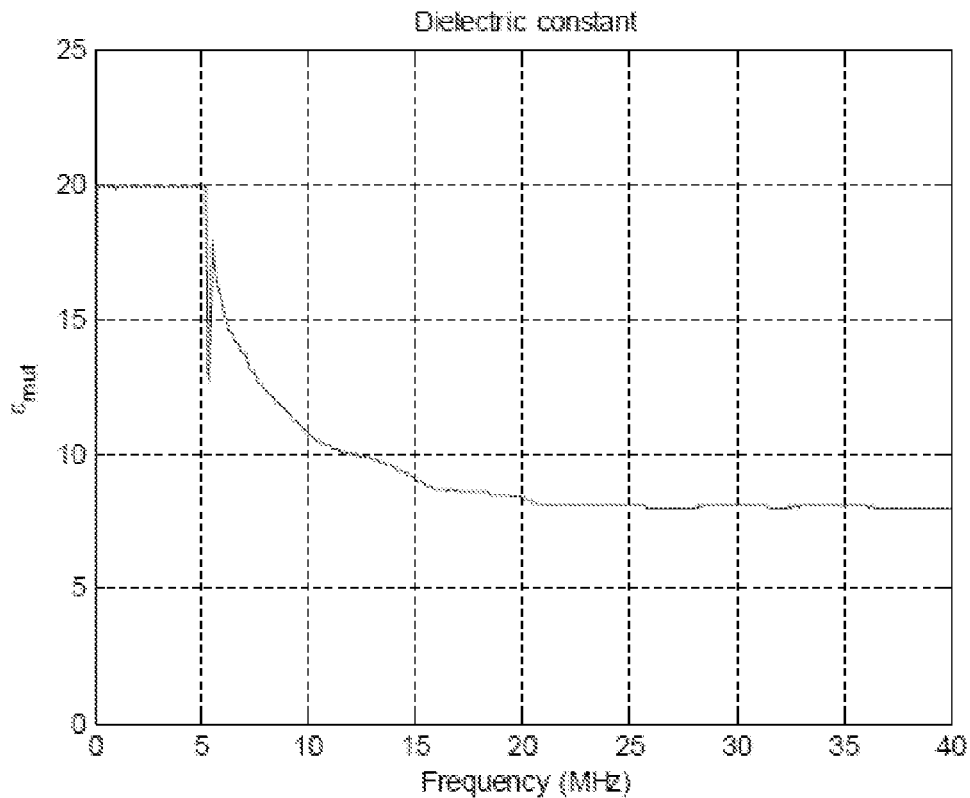
FIG. 44 is a graph showing the preliminary dielectric constant extraction in accordance with one embodiment of the present invention.
Figure 45:
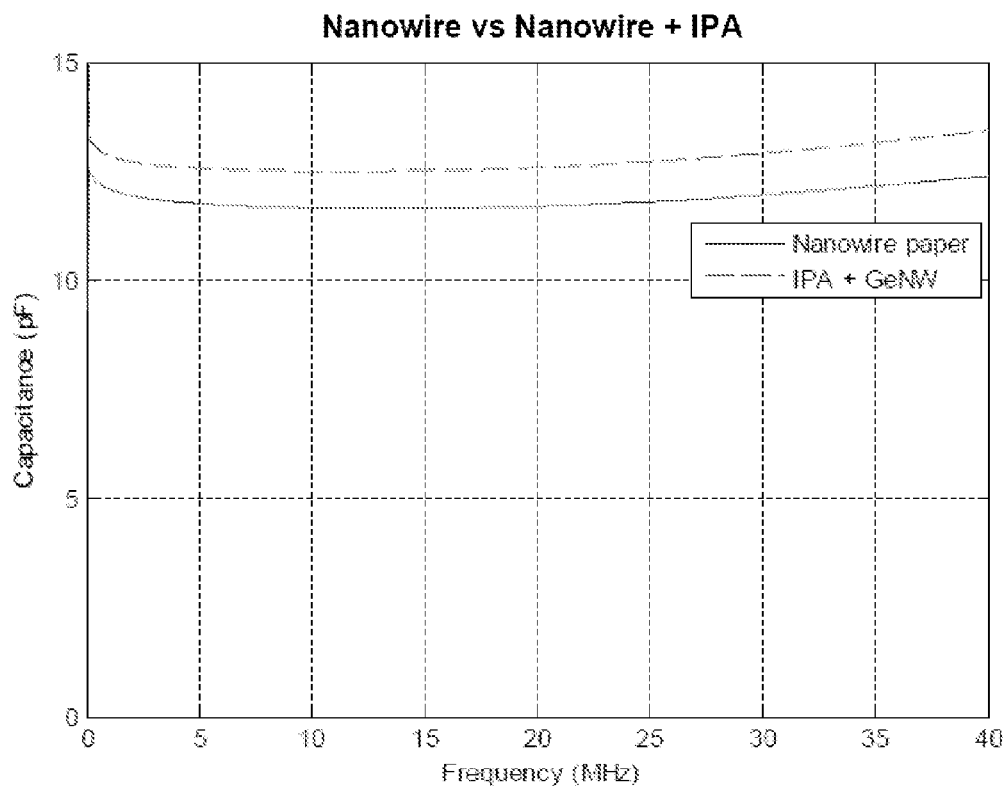
FIGS. 45-48 are graphs showing the capacitance (FIG. 45), the shunt conductance (FIG. 46), loss tangent (FIG. 47), and dielectric constant extraction (FIG. 48) of the nanowire paper as compared to the IPA and germanium nanowires in accordance with one embodiment of the present invention.
Figure 46:
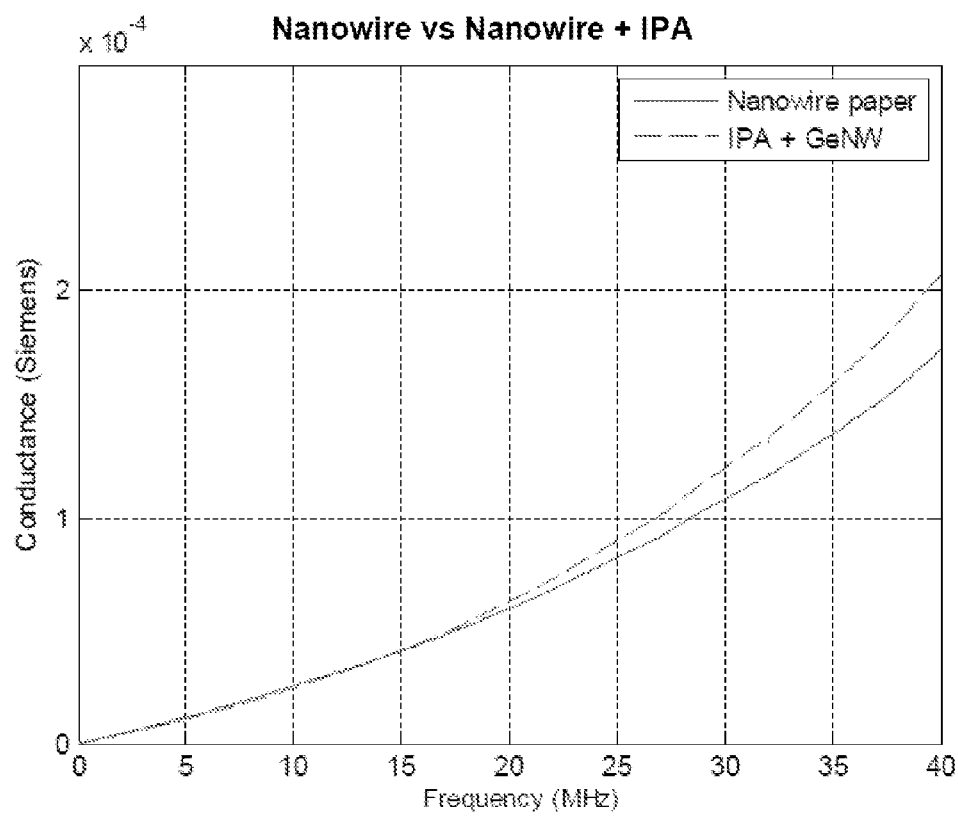
Figure 47:
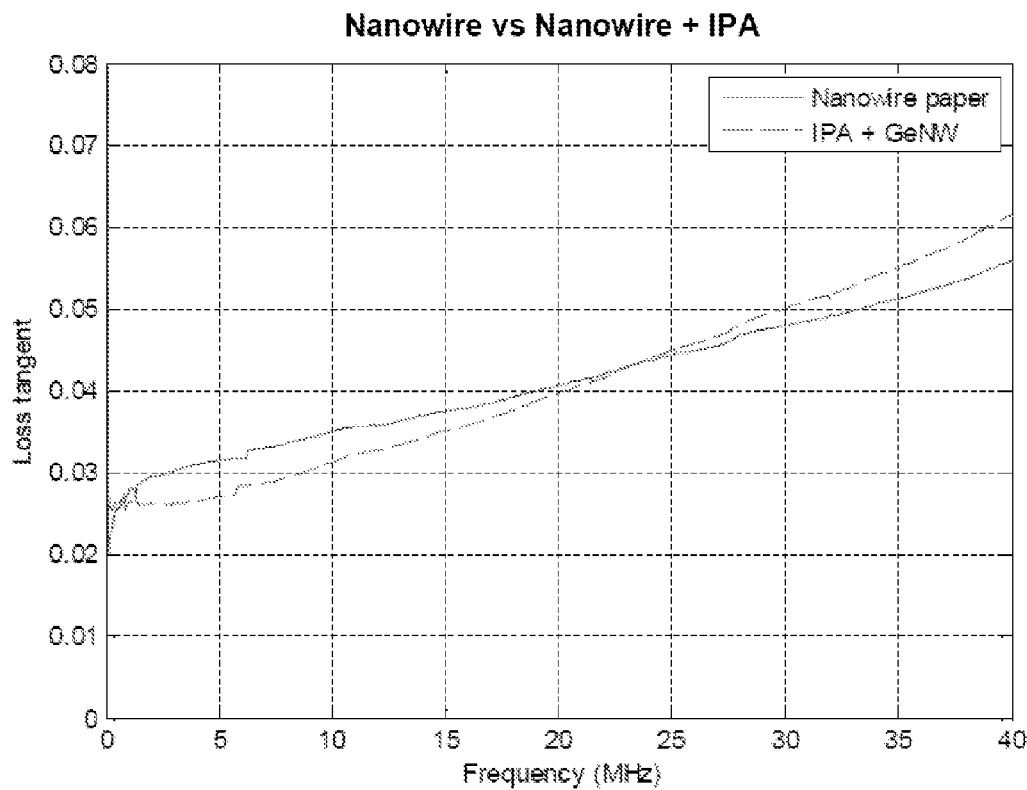
Figure 48:
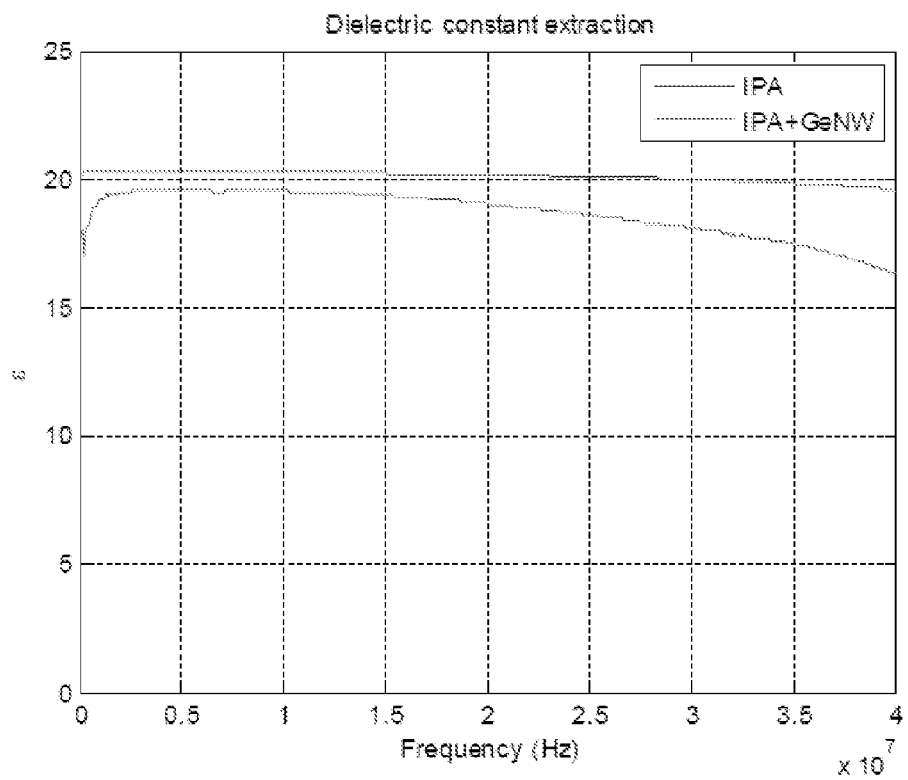

The sensor chip in FIG. 40 is an IDC sensor 3908. The chemical transducer component detects conductivity and dielectric constant, and is easily integrated with other lab-on-a-chip components. The IDC 3908 includes a pair of electrically conductive traces 4000s and 4000g formed on a substrate 102 wherein one of the electrically conductive traces is a signal electrode 4000s and the other electrically conductive trace is a ground electrode 4000g. A plurality of planar interdigitated capacitor electrodes 112 are electrically connected to the pair of electrically conductive traces 4000s and 4000g and formed on the elongated flexible substrate 102 within the gap. A high surface area material includes a conformal polymer coating to increase a sensitivity to the one or more materials. In this example, the electrode finger width is 100 μm and the finger spacing is 40 μm. The fields must "penetrate" the material-under-test (MUT). Extraction of material properties is hardest when the MUTs have widely varying conductivity. The loss tangent is determined using the equation: $\tan\delta = \sigma/\omega\cdot\varepsilon$. If the loss tangent is less than one ($\tan\delta < 1$), the material is a "dielectric." If the loss tangent is greater than one ($\tan\delta > 1$), the material is a "conductor." The high surface area material or nanowire mat layer has been previously described above. In this example, it is a "paper" that is "appliqué" to IDC substrate 102 by initial solvent wetting to apply the film. After solvent evaporation film remains strongly adhered. Pre-cast polymer films can be used with and without dispersed nano-wires. The pre-cast polymer films are also applied using solvent wetting process. FIGS. 41-43 are graphs showing the raw capacitance (FIG. 41), shunt conductance (raw) (FIG. 42), and loss tangent (ration of conduction current to displacement current) (FIG. 43) of the nanowire paper and air. FIG. 44 is a graph showing the preliminary dielectric constant extraction.

Figure 49:
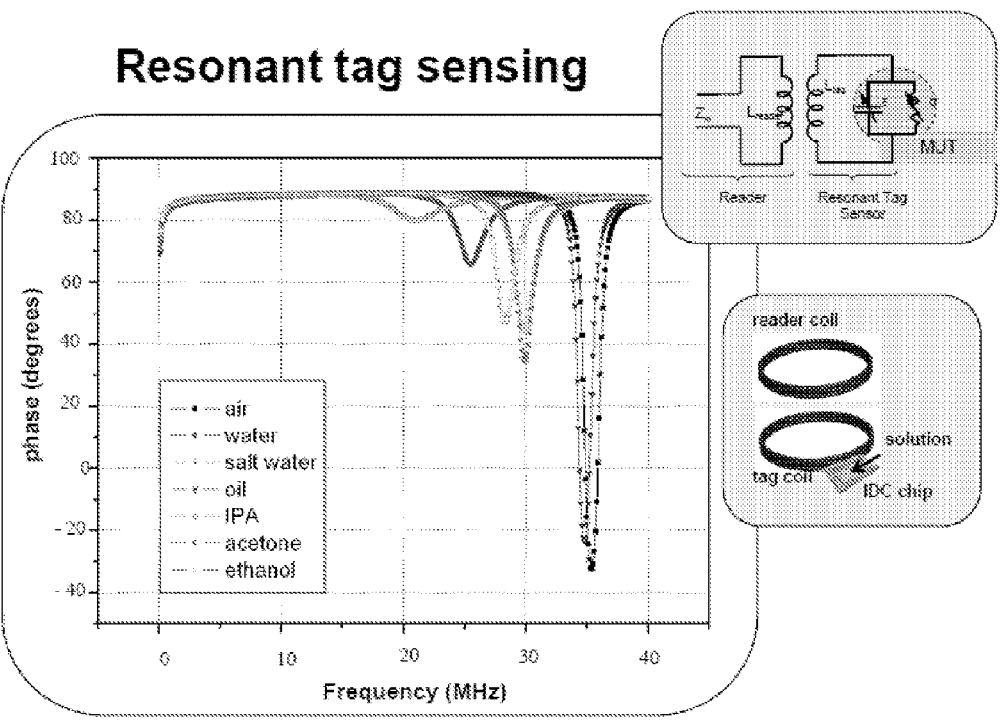
FIGS. 49-50 are graphs showing the resonant tag measurements for various non-contact and contact substances in accordance with one embodiment of the present invention.
Figure 50:
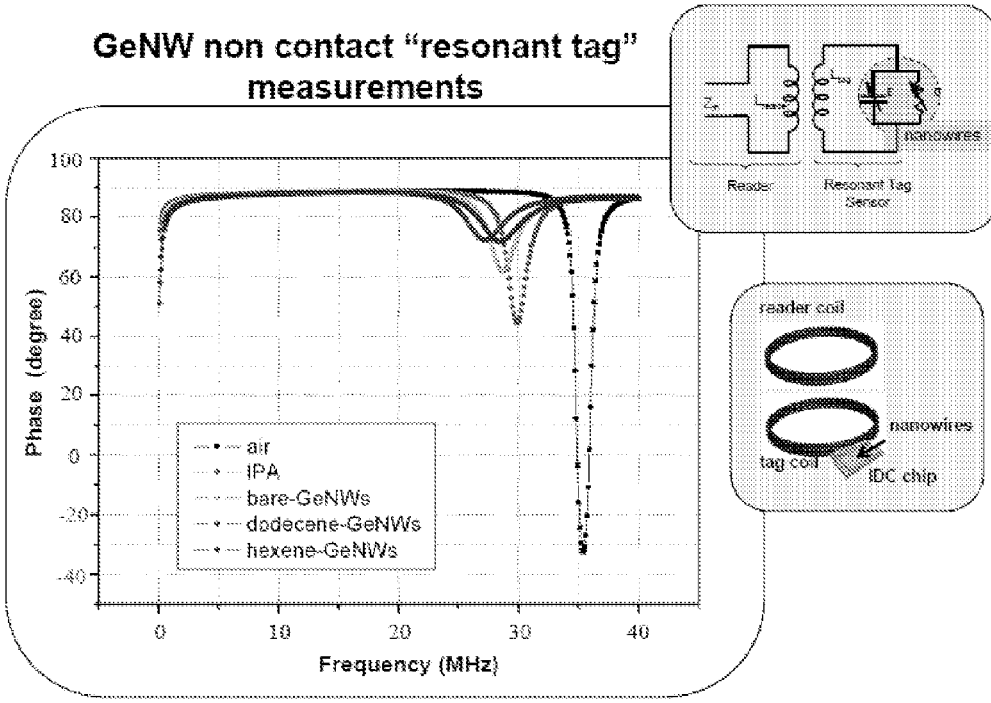

Two types of germanium nanowire mats were prepared for initial testing on the sensor device. One was prepared using iCVD/4-vinylpyridine. Another was prepared using poly-ethylene glycol (PEG) covalently bound to the nanowire surface. The nominal thickness of each mat's coating was 10 nm. Tests were performed in air (not submerged in the test liquid). The robustness of the mats were notably different. The iCVD mat was still robust. The PEG coated mat was quite brittle. Additionally, a test was performed after swelling/partially removing the iCVD coating with hexane solvent. FIGS. 45-48 are graphs showing the capacitance (FIG. 45), the shunt conductance (FIG. 46), loss tangent (FIG. 47), and dielectric constant extraction (FIG. 48) of the nanowire paper as compared to the IPA and germanium nanowires. FIGS. 49-50 are graphs showing the resonant tag measurements for various non-contact and contact substances.

Figure 51A:
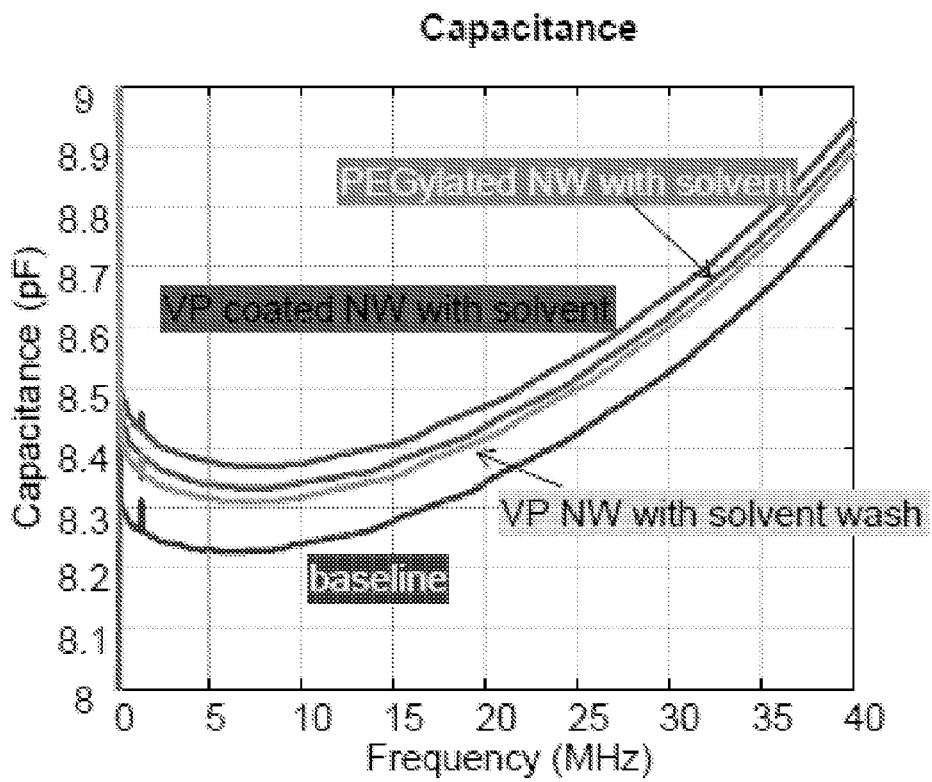
FIGS. 51A-B are graphs showing the capacitance and conductance measurements for the IDC sensor in accordance with one embodiment of the present invention.
Figure 51B:
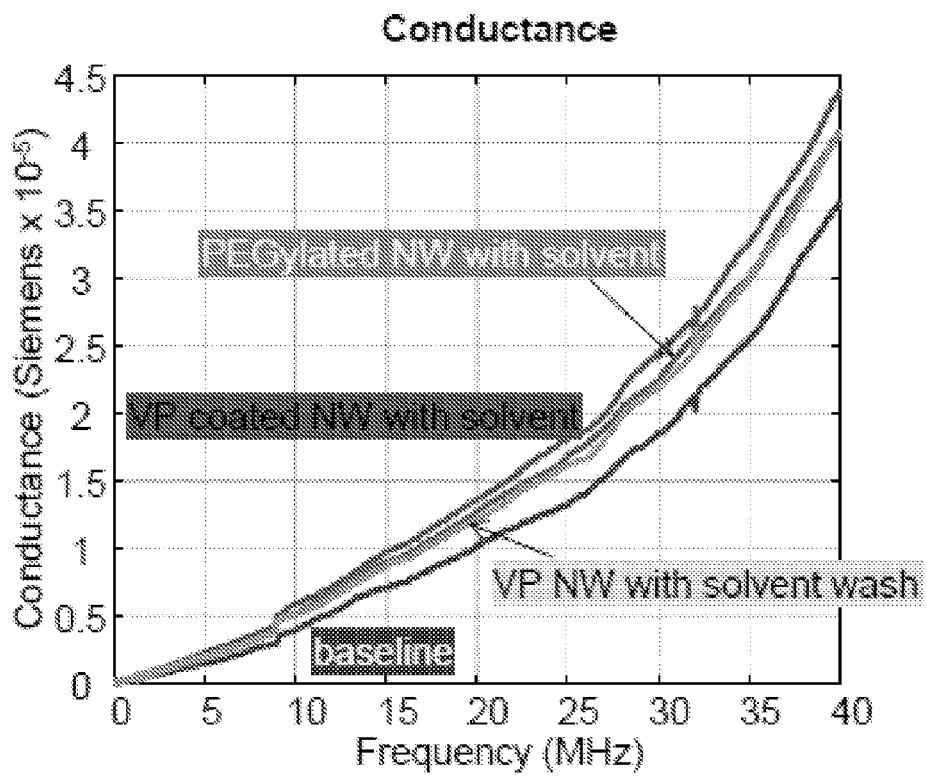

FIGS. 51A-B are graphs showing the capacitance and conductance measurements for the IDC sensor. The 10 micron-thick mats showed a small but measurable difference from the baseline (only air above the resonator). The mats were 'held' down by adding a drop of hexane (the solvent). The hexane wash was expected to partially dissolve and swell the VP polymer under the conditions applied. The Capacitance and conductance decreased as the polymer volume was removed.

A hybrid of these designs may also be used wherein a high surface area material is disposed on an elongated flexible substrate strip, a pair of electrically conductive traces and a plurality of planar interdigitated capacitor electrodes. The pair of electrically conductive traces are formed on the elongated flexible substrate proximate to a centerline of the elongated flexible substrate strip such that the pair of electrically conductive traces are parallel to one another and separated by a gap, the plurality of planar interdigitated capacitor electrodes formed on the elongated flexible substrate, the elongated flexible substrate strip rolled into a coil having a central void, and a ferrite core disposed within or through the central void of the coil. The plurality of planar interdigitated capacitor electrodes are electrically connected to the pair of electrically conductive traces and formed on the elongated flexible substrate within the gap. The high surface area material includes a conformal polymer coating to increase a sensitivity to the one or more materials.

Now referring to FIG. 52, taking measurements from the various sensors 5200 will now be described with respect to recovered fluids in the oil/gas industry. The flux alignment between the sensors 5200 in the fluid and the reader 5202 are essential. Flux confinement inside a solenoidal reader coil 5202 wrapped around a pipe 5204 is strongest of all configuration options. Placing the sensor 5200 inside a solenoidal reader coil 5202 will provide strongest possible coupling. Another example of a reader 5202 using parallel pipes 5204a, 5204b, 5204c is shown in FIG. 53. The reader coils 5202a, 5202b, 5202c are wrapped around the "pipes" 5204a, 5204b, 5204c, respectively, in which recovered fluids 5302 and sensors 5200 flow such that there is effectively a "zero" reader and sensor distance when the sensor 5200 is passing through. The pipe diameter can be optimized for sensor readout. The parallel pipes 5204a, 5204b, 5204c allow multiple sensor readout while increasing the total fluid flow rate. An instrument 5304 connected to the reader coils 5202a, 5202b, 5202c processes the data received from the reader coils 5202a, 5202b, 5202c.

As a result, the present invention provides a low cost, passive wireless dielectric constant and conductivity sensor with chemically sensitive coatings that can detect water and hydrocarbons in a down-hole environment including frac-fluid and oil.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

The invention claimed is:

1. A sensor for detecting one or more materials, the sensor comprising:
    a substrate;
    a passivation layer formed on the substrate;
    a self-resonant structure comprising:
        a planar spiral inductor disposed within the passivation layer, wherein the planar spiral inductor comprises an electrically conductive trace formed on the substrate in a planar spiral pattern having at least two turns and an inter-winding space between parallel segments of the electrically conductive trace, and
        a plurality of planar interdigitated capacitor electrodes disposed within the passivation layer, wherein the plurality of planar interdigitated capacitor electrodes are electrically connected to the electrically conductive trace of the planar spiral inductor and formed on the substrate within the inter-winding space of at least one outermost turn of the planar spiral inductor; and
    a high surface area material disposed on the passivation layer, wherein the high surface area material includes a conformal polymer coating to increase a sensitivity to the one or more materials.

2. The sensor as recited in claim 1, wherein the self-resonant structure is configured to have a capacitance and a conductance that is affected by a dielectric constant and a conductivity of the one or more materials when in contact with the self-resonant structure causing a change in a resonant frequency and a phase dip of the self-resonant structure.

3. The sensor as recited in claim 2, further comprising a non-contact inductively coupled reader coil suitable for detecting the change in the resonant frequency and the phase dip of the self-resonant structure.

4. The sensor as recited in claim 1, wherein the one or more materials comprise a hydrocarbon.

5. The sensor as recited in claim 1, further comprising a porous glass filter layer disposed on the high surface area material.

6. The sensor as recited in claim 1, wherein the high surface area material comprises a nonwoven nanowire mat or fabric of silicon or germanium nanowires, wherein the silicon or germanium nanowires are single-crystalline having a hydrophobic surface, an average diameter ranging from about 25 to 50 nm and an average length ranging from about 10 to 500 mm.

7. The sensor as recited in claim 1, further comprising:
    a cavity disposed within the substrate proximate to a center of the planar spiral inductor; and
    a ferrite core disposed in the cavity.

8. The sensor as recited in claim 1, wherein the substrate is a flexible substrate rolled to form a coil having a central void.

9. The sensor as recited in claim 8, further comprising a ferrite core disposed within or through the central void of the coil.

10. A sensor for detecting one or more materials, the sensor comprising:
    an elongated flexible substrate strip;
    a self-resonant structure comprising:
        an electrically conductive trace formed on the elongated flexible substrate proximate to a centerline of the elongated flexible substrate strip,
        the elongated flexible substrate strip is rolled into a coil having a central void, and
        a ferrite core disposed within or through the central void of the coil; and
    a high surface area material disposed on the elongated flexible substrate strip and the electrically conductive trace, wherein the high surface area material includes a conformal polymer coating to increase a sensitivity to the one or more materials.

11. The sensor as recited in claim 10, wherein the self-resonant structure is configured to have a capacitance and a conductance that is affected by a dielectric constant and a conductivity of the one or more materials when in contact with the self-resonant structure causing a change in a resonant frequency and a phase dip of the self-resonant structure.

12. The sensor as recited in claim 11, further comprising a non-contact inductively coupled reader coil suitable for detecting the change in the resonant frequency and the phase dip of the self-resonant structure.

13. The sensor as recited in claim 10, wherein the high surface area material has about 90% void space that allows high analyte penetration and strong capillary forces.

14. The sensor as recited in claim 10, wherein one or more surface properties of the high surface area material are selected to draw the one or more materials into the self-resonant structure.

15. The sensor as recited in claim 10, wherein the high surface area material comprises a nonwoven nanowire mat or fabric of silicon or germanium nanowires, wherein the silicon or germanium nanowires are single-crystalline having a hydrophobic surface, an average diameter ranging from about 25 to 50 nm and an average length ranging from about 10 to 500 mm.

16. The sensor as recited in claim 10, wherein the conformal polymer coating comprises a hexyl acrylate monomer, a benzyl methacrylate monomer, or an ethylene glycol diacrylate monomer.

17. A sensor for detecting one or more materials, the sensor comprising:
    an elongated flexible substrate strip;
    a self-resonant structure comprising:
        a pair of electrically conductive traces formed on the elongated flexible substrate proximate to a centerline of the elongated flexible substrate strip such that the pair of electrically conductive traces are parallel to one another and separated by a gap,
        a plurality of planar interdigitated capacitor electrodes formed on the elongated flexible substrate, wherein the plurality of planar interdigitated capacitor electrodes are electrically connected to the pair of electrically conductive traces and formed on the elongated flexible substrate within the gap,
        the elongated flexible substrate strip is rolled into a coil having a central void, and
        a ferrite core disposed within or through the central void of the coil; and
    a high surface area material disposed on the elongated flexible substrate strip, the pair of electrically conductive traces and the plurality of planar interdigitated capacitor electrodes, wherein the high surface area material includes a conformal polymer coating to increase a sensitivity to the one or more materials.

18. The sensor as recited in claim 17, wherein the self-resonant structure is configured to have a capacitance and a conductance that is affected by a dielectric constant and a conductivity of the one or more materials when in contact with the self-resonant structure causing a change in a resonant frequency and a phase dip of the self-resonant structure.

19. The sensor as recited in claim 18, further comprising a non-contact inductively coupled reader coil suitable for detecting the change in the resonant frequency and the phase dip of the self-resonant structure.

20. The sensor as recited in claim 17, wherein the high surface area material comprises a nonwoven nanowire mat or fabric of silicon or germanium nanowires.

* * * * *